(12) United States Patent
Ameer et al.

(10) Patent No.: US 12,171,910 B2
(45) Date of Patent: Dec. 24, 2024

(54) INTRAVASCULAR RETRIEVABLE CELL DELIVERY SYSTEM

(71) Applicant: Northwestern University, Evanston, IL (US)

(72) Inventors: Guillermo A. Ameer, Chicago, IL (US); Paul D. Puglisi, Evanston, IL (US)

(73) Assignee: Northwestern University, Evanston, IL (US)

( * ) Notice: Subject to any disclaimer, the term of this patent is extended or adjusted under 35 U.S.C. 154(b) by 964 days.

(21) Appl. No.: 16/612,540

(22) PCT Filed: May 11, 2018

(86) PCT No.: PCT/US2018/032354
§ 371 (c)(1),
(2) Date: Nov. 11, 2019

(87) PCT Pub. No.: WO2018/209259
PCT Pub. Date: Nov. 15, 2018

(65) Prior Publication Data
US 2020/0390938 A1 Dec. 17, 2020

Related U.S. Application Data

(60) Provisional application No. 62/504,905, filed on May 11, 2017.

(51) Int. Cl.
*A61L 27/38* (2006.01)
*A61F 2/02* (2006.01)
(Continued)

(52) U.S. Cl.
CPC .......... *A61L 27/3834* (2013.01); *A61F 2/022* (2013.01); *A61L 27/3808* (2013.01);
(Continued)

(58) Field of Classification Search
CPC .... A61F 2/022; A61F 2250/0039; A61F 2/07; A61F 2250/0068; A61F 2/06;
(Continued)

(56) References Cited

U.S. PATENT DOCUMENTS 5,312,380 A    8/1994   Alchas et al.
5,399,352 A *   3/1995   Hanson ..................... A61F 2/06
                                                                                        623/1.42
(Continued)

FOREIGN PATENT DOCUMENTS

WO    WO-0204039 A2 *   1/2002  ............... A61F 2/04
WO    WO-2006069027 A2 *   6/2006  ............... A61F 2/82
(Continued)

OTHER PUBLICATIONS

Ryan et al., Five-year follow-up after clinical islet transplantation. Diabetes. Jul. 2005;54(7):2060-9.
(Continued)

*Primary Examiner* — Brian E Pellegrino
(74) *Attorney, Agent, or Firm* — David W. Staple; Casimir Jones, S.C.

(57) ABSTRACT

Provided herein are intravascular retrievable cell delivery systems and methods of use thereof for cell transplantation.

11 Claims, 47 Drawing Sheets

(51) Int. Cl.
*A61F 2/07* (2013.01)
*A61L 27/52* (2006.01)
*A61L 27/54* (2006.01)
*C12N 5/071* (2010.01)

(52) U.S. Cl.
CPC ........... *A61L 27/3886* (2013.01); *A61L 27/52* (2013.01); *A61L 27/54* (2013.01); *C12N 5/0677* (2013.01); *A61F 2250/0039* (2013.01); *A61L 2300/43* (2013.01); *A61L 2300/64* (2013.01); *A61L 2400/06* (2013.01)

(58) Field of Classification Search
CPC ............. A61F 2250/0067; A61F 2/062; A61L 27/3808; A61L 27/3834; C12N 5/0677
USPC .................................................. 623/1.41, 1.3
See application file for complete search history.

(56) References Cited

U.S. PATENT DOCUMENTS

| | | | |
|---|---|---|---|
| 7,326,238 B1* | 2/2008 | Kilpatrick | A61L 27/3808 623/1.42 |
| 9,205,177 B2* | 12/2015 | Schorgl | A61F 2/07 623/1.42 |
| 2007/0123973 A1* | 5/2007 | Roth | A61L 31/16 623/1.15 |
| 2009/0105805 A1 | 4/2009 | Baker et al. | |
| 2009/0105811 A1* | 4/2009 | Dinh | A61F 2/07 623/1.41 |
| 2011/0004230 A1 | 1/2011 | Levine et al. | |
| 2015/0157444 A1 | 6/2015 | Cully et al. | |
| 2016/0346382 A1 | 12/2016 | Bryce et al. | |

FOREIGN PATENT DOCUMENTS

| | | | | |
|---|---|---|---|---|
| WO | WO-2016183277 A1* | 11/2016 | | A61K 38/39 |
| WO | WO 2017/062757 | 4/2017 | | |

OTHER PUBLICATIONS

Shapiro et al., International trial of the Edmonton protocol for islet transplantation. N Engl J Med. Sep. 28, 2006;355(13):1318-30.
Shapiro et al., Islet transplantation in seven patients with type 1 diabetes mellitus using a glucocorticoid-free immunosuppressive regimen. N Engl J Med. Jul. 27, 2000;343(4):230-8.
International Search Report and Written Opinion for PCT/US2018/032354 mailed Oct. 15, 2018, 13 pages.

* cited by examiner

A)

B)

C)

A)

B)

C)

A)

B)

C)

C)

D)

Completed Rodent Prototypes

Rodent Prototype 1

Rodent Prototype 2

Rodent Prototype 3

Rodent Prototype 4

Rodent Prototype 5

FIG. 27A    FIG. 27B
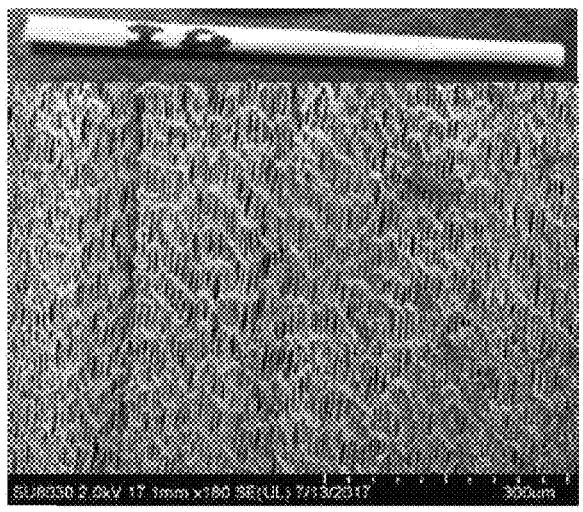 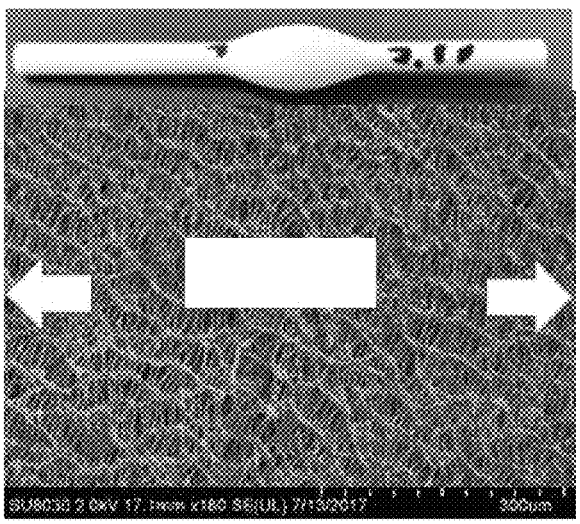
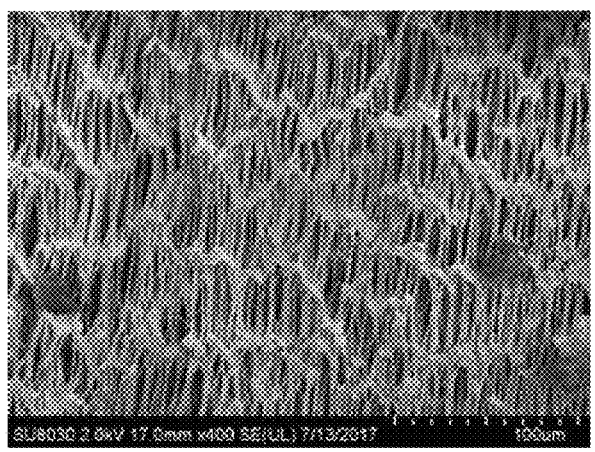 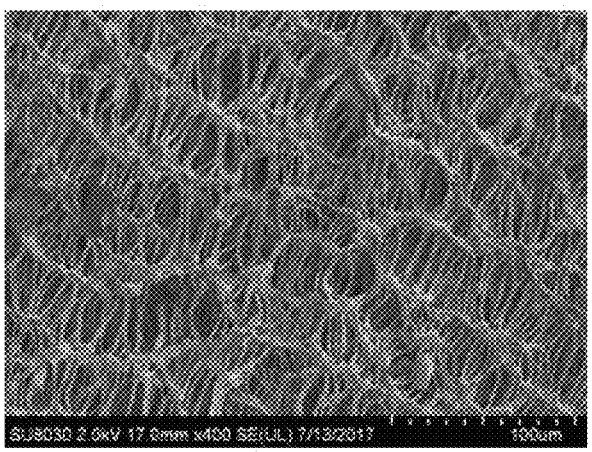
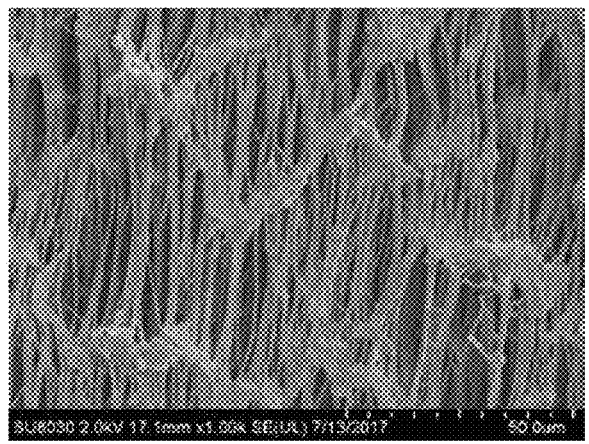 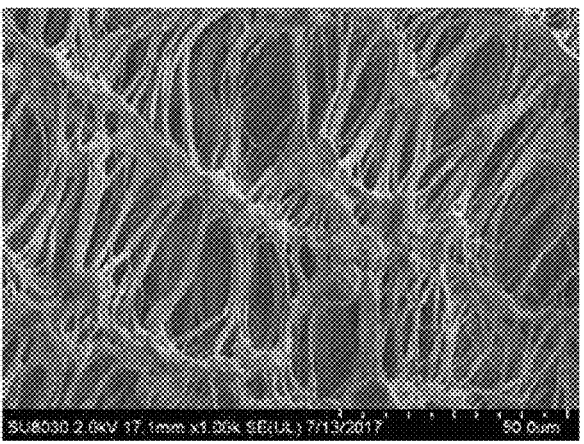

Stented Vascular Graft Design

Front view 3D view

Side view

FIG. 32

- $Vo = \pi * L * (ro^{\wedge}2 - ri^{\wedge}2)$
  - 1.5 mm ePTFE graft ID
  - 10 mm length
  - 2 mm stent ID
  - Deformation length = 5 mm
  - Deformation ID = 2.65 mm
- $Vo = \pi * 5 * ((2.65/2)^{\wedge}2 - (2/2)^{\wedge}2) = 11.8693$ mm$^3$
- 122 micron diameter for islets from Lewis rats[12]
  - $Vi = 4/3 * \pi * r^{\wedge}3 = 4/3 * \pi * (.122/2)^{\wedge}3 = 9.508 * 10^{\wedge}-4$ mm$^3$ per islet
- 11.8693 mm$^3$ / 9.508*10$^{\wedge}$-4 mm$^3$ per islet = 12483 islets held in device (no PPCN/additives)

FIG. 33

| Study Group | TG1 | TG1 | TG1 | TG2 | TG2 | TG2 | TG3 | TG3 | TG3 |
|---|---|---|---|---|---|---|---|---|---|
| Rat Number | Rat 1 | Rat 2 | Rat 3* | Rat 4 | Rat 5 | Rat 6 | Rat 7 | Rat 8 | Rat 9 |
| Surgery Sucessful (Day 0) | | | | | | | | | |
| Week 1 Ultrasound (Day 7) | | | | | | | | | |
| Week 2 Ultrasound (Day 14) | | | | | | | | | |
| Week 3 Ultrasound (Day 21) | | | | | | | | | |
| Euthanasia and Tissue Collection (Day 28) | | | | | | | | | |

A)

B)

C)

D)

INTRAVASCULAR RETRIEVABLE CELL DELIVERY SYSTEM

CROSS-REFERENCE TO RELATED APPLICATION

The present application is a § 371 National Entry Application of PCT/US2018/032354, filed May 11, 2018, which claims priority to U.S. Provisional Patent Application Ser. No. 62/504,905 filed May 11, 2017, each of which is hereby incorporated by reference in its entirety.

FIELD

Provided herein are intravascular retrievable cell delivery systems and methods of use thereof for cell transplantation.

BACKGROUND

Two current strategies are being employed in hospitals and research institutions across the globe today in order to cure Type 1 Diabetes (T1D). The first is a pancreas transplant. Although this surgery has been effective at curing T1D, the number of pancreas transplants performed per year is low due to organ donor shortage and the selection criteria for viable donor pancreas. The second strategy to cure T1D is islet transplantation. Islets are normally transplanted into the liver or hepatic portal vein in this procedure, often resulting in low islet survival rates due to acute inflammatory responses, oxidative stress, and abnormal blood flow. Therefore, new technologies are needed in order to provide a stable and suitable environment for islets to survive and perform their necessary function of producing insulin and regulating metabolic glucose in T1D patients.

SUMMARY

Provided herein are intravascular retrievable cell delivery systems and methods of use thereof for cell transplantation.

In some embodiments, provided herein are devices for the intravascular transplantation of cargo (e.g., cells, drugs, etc.) comprising: (a) an outer graft, the outer graft comprising an inner lumen and an outer wall, wherein the outer graft comprises first and second terminal portions and a central expanded portion, the central portion having a greater inner cross-sectional area than the terminal portions; (b) an inner element, the inner element comprising an inner lumen and an outer wall; wherein the inner element comprises a cross-sectional size and shape along its entire length that allows the inner element to fit within the lumen of the outer graft; and wherein the inner element is configured for insertion into the inner lumen of the outer graft, and wherein when the inner element resides within the outer graft, a void exists between all or a portion of the inner element and all or a portion of the outer graft. In some embodiments, the inner element is an inner graft. In some embodiments, the inner graft resides within the outer graft, the inner graft extends from the first terminal portion of the outer graft to the second terminal portion of the outer graft. In some embodiments, the outer wall of the inner graft approximates the inner cross-sectional area of the terminal portions of the outer graft. In some embodiments, the inner element is a flow diverter. In some embodiments, the inner element is an inner stent. In some embodiments, when the inner stent resides within the outer graft, the inner graft extends from the first terminal portion of the outer graft to the second terminal portion of the outer graft. In some embodiments, when the inner stent resides within the outer graft, the inner stent resides completely within the central expanded portion of the outer graft. In some embodiments, the outer wall of the outer graft is configured for contacting the inner lumen of the vasculature of a subject. In some embodiments, the inner lumen of the outer graft and the outer wall of the inner element are configured to interact to hold the inner element in place within the outer graft. In some embodiments, the inner lumen of the inner element is configured to allow blood to flow through the inner lumen, when inserted into the vasculature of a subject. In some embodiments, the inner element is permeable or semipermeable. In some embodiments, the inner element is configured to allow fluids, nutrients, peptides, and/or proteins to pass between the inner lumen of the inner element and the void between the inner element and the outer graft.

In some embodiments, provided herein are intravascular delivery systems comprising: (a) a device for the intravascular transplantation of cargo (e.g., cells, drugs, etc.) described herein; and (b) a carrier material, wherein the carrier material resides within the void between the inner element and the outer graft of the device. In some embodiments, the intravascular delivery system further comprises: (c) a cargo embedded with the carrier material. In some embodiments, the cargo is selected from transplantable cells or a therapeutic agent. In some embodiments, the cargo comprises transplantable cells selected from islets cells, stem cells, hepatocytes, and renal tubular cells. In some embodiments, the transplantable cells are pancreatic islet cells and the inner graft is permeable to insulin.

In some embodiments, the cargo comprises a therapeutic agent selected from insulin, a hormone, and an anticoagulant. In some embodiments, the carrier material is a polymer-based material. In some embodiments, the carrier material is biocompatible. In some embodiments, the carrier material comprises a synthetic polymer, a natural polymer, and/or non-polymeric components. In some embodiments, the carrier material comprises a thermoresponsive polymer. In some embodiments, the carrier material comprises poly (polyethyleneglycol citrate-co-N isopropylacrylamide) (PPCN). In some embodiments, the intravascular delivery system further comprises endothelial cells adhered to the inner lumen of the inner graft.

In some embodiments, provided herein are devices for the intravascular transplantation of cells comprising: (a) an inner element (e.g., graft, stent, flow diverter, etc.), the inner element (e.g., graft, stent, flow diverter, etc.) comprising a cylindrical shape with an inner lumen and an outer wall; (b) an outer graft, the outer graft comprising an inner lumen and an outer wall; wherein the inner element (e.g., graft, stent, flow diverter, etc.) is configured for insertion into the inner lumen of the outer graft, and wherein when the inner element (e.g., graft, stent, flow diverter, etc.) resides within the outer graft, a void exists between all or a portion of the inner element (e.g., graft, stent, flow diverter, etc.) and all or a portion of the outer graft.

In some embodiments, provided herein are devices for the intravascular transplantation of cells comprising: (a) an inner element (e.g., graft, stent, flow diverter, etc.), the inner element (e.g., graft, stent, flow diverter, etc.) comprising a cylindrical shape with an inner lumen and an outer wall; (b) an outer graft, the outer graft comprising an inner lumen and an outer wall, wherein the outer graft comprises a cylindrical shape at its terminal portions and an expanded central portion; wherein the inner element (e.g., graft, stent, flow diverter, etc.) is configured for insertion into the outer graft such that the outer wall of the inner element (e.g., graft, stent, flow diverter, etc.) approximates the inner lumen of the terminal portions of the outer graft, and wherein when the inner element (e.g., graft, stent, flow diverter, etc.) resides within the lumen of the out graft the expanded central portion creates a void between the inner element (e.g., graft, stent, flow diverter, etc.) and the outer graft.

In some embodiments, the outer wall of the other graft is configured for contacting the inner lumen of the vasculature of a subject. In some embodiments, the inner lumen of the outer graft and the outer wall of the inner element (e.g., graft, stent, flow diverter, etc.) are configured to interact to hold the inner element (e.g., graft, stent, flow diverter, etc.) in place within the outer graft. In some embodiments, the inner lumen of the inner element (e.g., graft, stent, flow diverter, etc.) is configured to allow blood flow through the inner lumen, when inserted into the vasculature of a subject. In some embodiments, the inner element (e.g., graft, stent, flow diverter, etc.) is permeable. In some embodiments, the inner element (e.g., graft, stent, flow diverter, etc.) is configured to allow fluids, nutrients, peptides, metabolites, and proteins pass between the inner lumen of the inner element (e.g., graft, stent, flow diverter, etc.) and the void between the inner element (e.g., graft, stent, flow diverter, etc.) and the outer graft.

In some embodiments, provided herein are intravascular cell delivery system comprising: (a) a device for the intravascular transplantation of cells, as described herein, wherein the inner element (e.g., graft, stent, flow diverter, etc.) is within the outer graft; (b) a carrier material, wherein the carrier material resides within the void between the inner element (e.g., graft, stent, flow diverter, etc.) and the outer graft; and (c) transplantable cells, wherein the transplantable cells are embedded within the carrier material. In some embodiments, the carrier material is a polymer-based material. In some embodiments, the carrier material is biocompatible. In some embodiments, the carrier material comprises a synthetic polymer, a natural polymer, and/or non-polymeric components. In some embodiments, the carrier material comprises a thermoresponsive polymer. In some embodiments, the carrier material comprises PPCN (aka NANONETS). In some embodiments, the transplantable cells are selected from pancreatic islet cells, stem cells, hepatocytes, or renal tubular cells. In some embodiments, the transplantable cells are pancreatic islet cells and the inner element (e.g., graft, stent, flow diverter, etc.) is permeable to insulin. In some embodiments, systems further comprise endothelial cells adhered to the inner lumen of the inner element (e.g., graft, stent, flow diverter, etc.).

In some embodiments, provided herein are methods of cell transplantation comprising implanting a system described herein into the vasculature of a subject.

In some embodiments, provided herein are methods of treating disease (e.g., T1D) comprising transplanting a system described herein into the vasculature of a subject.

BRIEF DESCRIPTION OF THE DRAWINGS

FIG. 27. SEM images of a 2.1 mm inner diameter undeformed control ePTFE vascular graft (left) and an experimental ePTFE vascular graft that was inflated and deformed by a balloon catheter in the East-West direction (right) at first, second, and third magnifications.

FIG. 32. The vascular graft dimensions and calculations for the volume of the concentric midsection that could be stored in the TG3 vascular implant for the in vivo rat study. The formulas used are volume of a hollow cylinder for the vascular graft concentric midsection volume and volume of a sphere for the individual rat islet volume.

FIG. 33. In vivo study timeline for the implantation of the Intravascular Retrievable Cell Delivery System for Islet Transplantation into Sprague-Dawely Rats using the Abdominal Aorta Interposition Model. Gray indicates successful completion of the timeline event. Black indicates the timeline event was unable to be completed. Rat 7 passed away from an unknown cause of death between the week 2 and 3 ultrasound time point and was unable to complete the study. (*=initial rodent passed away from anesthesia overdose and was immediately replaced).

Definitions

Figure 1:
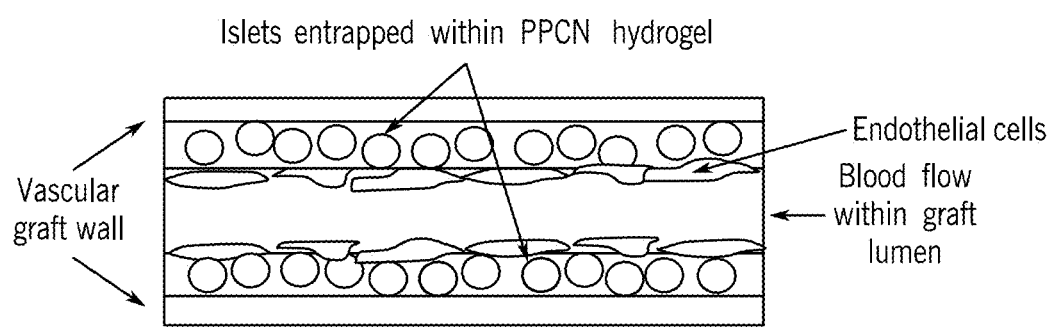
FIG. 1. An exemplary schematic depicting a portion of outer and inner grafts, the void space between the grafts, PPCN embedded islet cells, and endothelial cells coated on the inner lumen of the inner graft.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "an islet cell" is a reference to one or more islet cells and equivalents thereof known to those skilled in the art, and so forth.

As used herein, the term "and/or" includes any and all combinations of listed items, including any of the listed items individually. For example, "A, B, and/or C" encompasses A, B, C, AB, AC, BC, and ABC, each of which is to be considered separately described by the statement "A, B, and/or C." As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "substantially all," "substantially complete" and similar terms refer to greater than 99%; and the terms "substantially none," "substantially free of" and similar terms refer to less than 1%.

The term "about" allows for a degree of variability in a value or range. As used herein, the term "about: refers to values within 10% of the recited value or range (e.g., about 50 is the equivalent of 45-55).

As used herein, the term "biocompatible" refers to materials, compounds, or compositions means that do not cause or elicit significant adverse effects when administered to a subject. Examples of possible adverse effects that limit biocompatibility include, but are not limited to, excessive inflammation, excessive or adverse immune response, and toxicity.

As used herein, the term "biostable" refers to compositions or materials that do not readily break-down or degrade in a physiological or similar aqueous environment.
Conversely, the term "biodegradeable" refers herein to compositions or materials that readily decompose (e.g., depolymerize, hydrolyze, are enzymatically degraded, disassociate, etc.) in a physiological or other environment.

As used herein, the phrase "physiological conditions" relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

As used herein, the term "hydrogel" refers to a three-dimensional (3D) crosslinked network of hydrophilic polymers that swells, rather than being dissolved, in water.

As used herein, the term "thermoresponsive" refers to material that exhibit altered physical characteristics at different temperature ranges. Particularly relevant herein are "phase-transitioning thermoresponsive" materials. Phase-transitioning thermoresponsive" materials are soluble or in a liquid state at a first temperature range (e.g., below 26° C.) and insoluble or in a solid state at a second temperature range (e.g., 30-45° C.).

As used herein, the term permeable refers to the characteristic of a material allowing liquids and solutes such as small molecules, nutrients, drugs, peptides, and some proteins (e.g., under a size threshold) to pass through.

DETAILED DESCRIPTION

Provided herein are intravascular retrievable cell delivery systems and methods of use thereof for cell transplantation.

In some embodiments, provided herein are intravascular graft devices and systems for implantation into the vasculature of a subject. In some embodiments, the graft devices contain transplantable cells or other cargo (e.g., therapeutic agents) that reside within the device and interact with blood flowing through the device to receive nutrients and other components from the blood, and to deliver materials/agents from the transplanted cells. For example, when a device comprising pancreatic islet cells embedded within a hydrogel carrier is transplanted into the vasculature of a subject, the blood supplies the islet cells with nutrients, metabolites, etc. (e.g., oxygen, glucose, etc.), and insulin secreted from the islet cells is supplied to the blood. For other cell types, analogous transfers of metabolites and secreted materials occurs. In some embodiments, rather than, or in addition to, having cells embedded in a carrier, a pharmaceutical or other bioactive agent is embedded within the carrier (within the device) and exchanges with the blood.

In some embodiments, devices herein comprise inner and outer elements (See Figures herein). In some embodiments, the inner element (e.g., graft, stent, flow diverter, etc.) is sized to reside within the outer graft. In some embodiments, a portion of the exterior of the inner element (e.g., graft, stent, flow diverter, etc.) contacts the interior of the outer graft. In some embodiments, contact between the inner and outer grafts holds the inner element (e.g., graft, stent, flow diverter, etc.) in place within the outer graft. In some embodiments, the outer graft comprises an expanded section (e.g., expanded cross-section). In some embodiments, the expanded section of the outer graft creates a void between the outer and inner element (e.g., graft, stent, flow diverter, etc.). It is within this void that a carrier material (e.g., hydrogel (e.g., PPCN)) embedded cells or other transplantable/deliverable agents is contained. In some embodiments, rather than having an expanded portion of the outer graft, the inner lumen of the outer graft is large enough to encompass the inner element (e.g., graft, stent, flow diverter, etc.) while maintaining a void space between the inner and outer grafts (FIG. 1).

In some embodiments, grafts are of any suitable material for graft and/or implant materials. In some embodiments, the grafts are biostable. In some embodiments, the grafts can be formed from biocompatible materials known to one skilled in the art. For example, vascular grafts can be formed from poly(ethylene terephthalate) (PETE, Dacron™) or poly(tetrafluoroethylene), such as expanded poly(tetrafluoroethylene) (ePTFE). In some embodiments, the grafts comprise expanded polytetrafluoroethylene (ePTFE).

In some embodiments, provided herein are stents (e.g., vascular stents). In some embodiments, the stent is configured to reside within a graft described herein. The stent can be formed from biocompatible materials known to one skilled in the art. Vascular stents can be formed from stainless steel, a cobalt-chromium alloy, a cobalt-chromium-molybdenum (CoCrMo) alloy, titanium alloy, commercially pure Ti (cpTi), medical grade stainless steel, tantalum, tantalum alloy, nitinol, polymers, plastic, ceramics, oxides, minerals, glasses and combinations thereof.

In some embodiments, the retrievability of the systems herein is achieved by containment of the transplanted cells with the device. In some embodiments, cells contained within the systems herein are placed within the lumen the vasculature. In some embodiments, the intravascular islets graft is a non-obstructive vascular interposition graft that enhances the supply of oxygen to the islets. In some embodiments, this system provides surgeons with options regarding the anastomotic locations within the body's vascular system that facilitates one or more of the following: create the least disturbance to the native blood flow, allow easy implant and explant, maximize islet functionality (e.g., due to improved oxygenation, due to protection from deleterious blood flow dynamics, etc.), etc.

In some embodiments, devices and systems described herein comprise transplantable cells (e.g., pancreatic islet cells) entrapped/embedded/residing within a biocompatible polymer-based material. For example, in some embodiments, the gap between the inner and outer grafts, created by the expanded portion of the devices described above, contains a biocompatible polymer-based material with transplantable cells embedded therein.

In some embodiments, a polymer-based material comprises a synthetic polymer selected from a polyester, poly (diol citrate) (e.g., butanediol, hexanediol, octanediol, decanediol, dodecanediol, hexadecanediol, etc.), poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, or co-polymers or composites thereof. In some embodiments, the polymer-based material comprises a natural polymer, such as polysaccharides and proteins. Non-limiting examples of suitable polysaccharides include starch, amylose, amylopectin, cellulose, arabinoxylan, chitin, chitinosan, pectin, alginate, carageenan, dextrin, gums (e.g., arabic gum, gellan gum, guar gum, locust bean gum, xanthan gum), or combinations thereof. Examples of suitable proteins include but are not limited to serum albumin, egg albumin, casein, collagen, gelatin, soy protein, whey protein, zein, or combinations thereof. In some embodiments, the polymer-based materials comprise a combination of natural polymers, synthetic polymers, and/or other components (e.g., fillers, small molecules, peptides, crosslinkers, etc.).

In some embodiments, the polymer-based material comprises a thermoresponsive polymer material. In some embodiments, the polymer-based material comprises the thermoresponsive citrate-based hydrogel, poly(polyethyleneglycol citrate-co-N isopropylacrylamide) (PPCN). In some embodiments, PPCN provides a suitable microenvironment to support cell (e.g., islet) viability and function. In some embodiments, the polymer based material comprises a PPCN hydrogel. PPCN allows for the encapsulation of transplantable cells (e.g., islet cells). In some embodiments, PPCN allows for entrapment and/or supply of soluble factors to preserve the function of the embedded cells. In some embodiments, PPCN allows for release of factors (e.g., insulin) produced by the embedded cells.

In some embodiments, the polymer-based material comprises PPCN or another polymer comprising at least 0.1% citric acid monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% citric acid monomers (e.g., <99%, <98%, <95%, <90%, <80%, <70%, <60%, <50%, <40%, <30%, <20%,<10%, <5%,<4%, <3%, <2%, <1%, <0.5%,). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% citric acid monomers.

In some embodiments, the polymer-based material comprises PPCN or another polymer comprising at least 0.1% polyethylene glycol monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% polyethylene glycol monomers (e.g., <99%, <98%, <95%, <90%, <80%, <70%, <60%, <50%, <40%, <30%, <20%,<10%, <5%,<4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% polyethylene glycol monomers.

In some embodiments, the polymer-based material comprises PPCN or another polymer comprising at least 0.1% glycerol 1,3-diglycerolate diacrylate monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% glycerol 1,3-diglycerolate diacrylate monomers (e.g., <99%, <98%, <95%, <90%, <80%, <70%, <60%, <50%, <40%, <30%, <20%,<10%, <5%,<4%, <3%, <2%, <1%, <0.5%,). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% glycerol 1,3-diglycerolate diacrylate monomers.

In some embodiments, the polymer-based material comprises PPCN or another polymer comprising at least 0.1% N-isopropylacrylamide monomers (e.g., >0.1%, >0.2%, >0.5%, >1%, >2%, >3%, >4%, >5%, >10%, >20%, >30%, >40%, >50%, >60%, >70%, >80%, >90%, >95%, >98%, >99%). In some embodiments, polymers herein comprise less than 99% N-isopropylacrylamide monomers (e.g., <99%, <98%, <95%, <90%, <80%, <70%, <60%, <50%, <40%, <30%, <20%,<10%, <5%,<4%, <3%, <2%, <1%, <0.5%). In some embodiments, polymers comprise about 99%, about 98%, about 95%, about 90%, about 80%, about 70%, about 60%, about 50%, about 40%, about 30%, about 20%, about 10%, about 5%, about 4%, about 3%, about 2%, about 1%, or about 0.5% N-isopropylacrylamide monomers.

In some embodiments, the PPCN-based materials described herein are liquid at sub-physiologic temperatures (e.g., 36° C., 35° C., 34° C., 33° C., 32° C., 31° C., 30° C., 29° C., 28° C., 27° C., 26° C., 25° C., 24° C., 23° C., 22° C., 21° C., 20° C., or lower or ranges therebetween). In some embodiments, the PPCN-based materials described herein gel at or near physiologic temperatures (e.g., 30° C., 31° C., 32° C., 33° C., 34° C., 35° C., 36° C., 37° C., 38° C., 39° C., 40° C., or ranges therebetween).

In some embodiments, the devices and system herein find use with a wide variety of transplantable cells, not limited to stem cells, progenitor cells, islets (islet clusters), hepatocytes, and renal cells. In some embodiments, the carrier material within the devices and systems herein comprises bioactive agents (e.g. cytokines, growth factors, pharmaceuticals, etc.) for administration to a subject (e.g., instead of the cells described in embodiments herein, in addition to cells).

The methods, devices, and systems described herein provide, for example: vascular graft delivery systems for islets; vascular graft delivery system for other cell types such as hepatocytes (liver cells) or renal tubular cells (kidney cells), among others; vascular graft delivery systems for hydrogels or other synthetic or natural materials; vascular graft delivery systems for growth factors, cytokines, and other bioactive agents; etc.

The methods, devices, and systems described herein provide: (1) suitable microenvironment conditions for islets cells (or other transplantable cells) to live and function; (2) increased protection of islets cells from deleterious effects of blood flow dynamics; (3) additional options of surgical implantation sites for the surgeon throughout the vascular system; (4) easy implantation as well explantation inside the vascular system; and/or (5) the optional addition of a hydrogel, growth factors, cytokines, etc. alongside islet cell clusters inside of the vascular graft.

Figure 36:
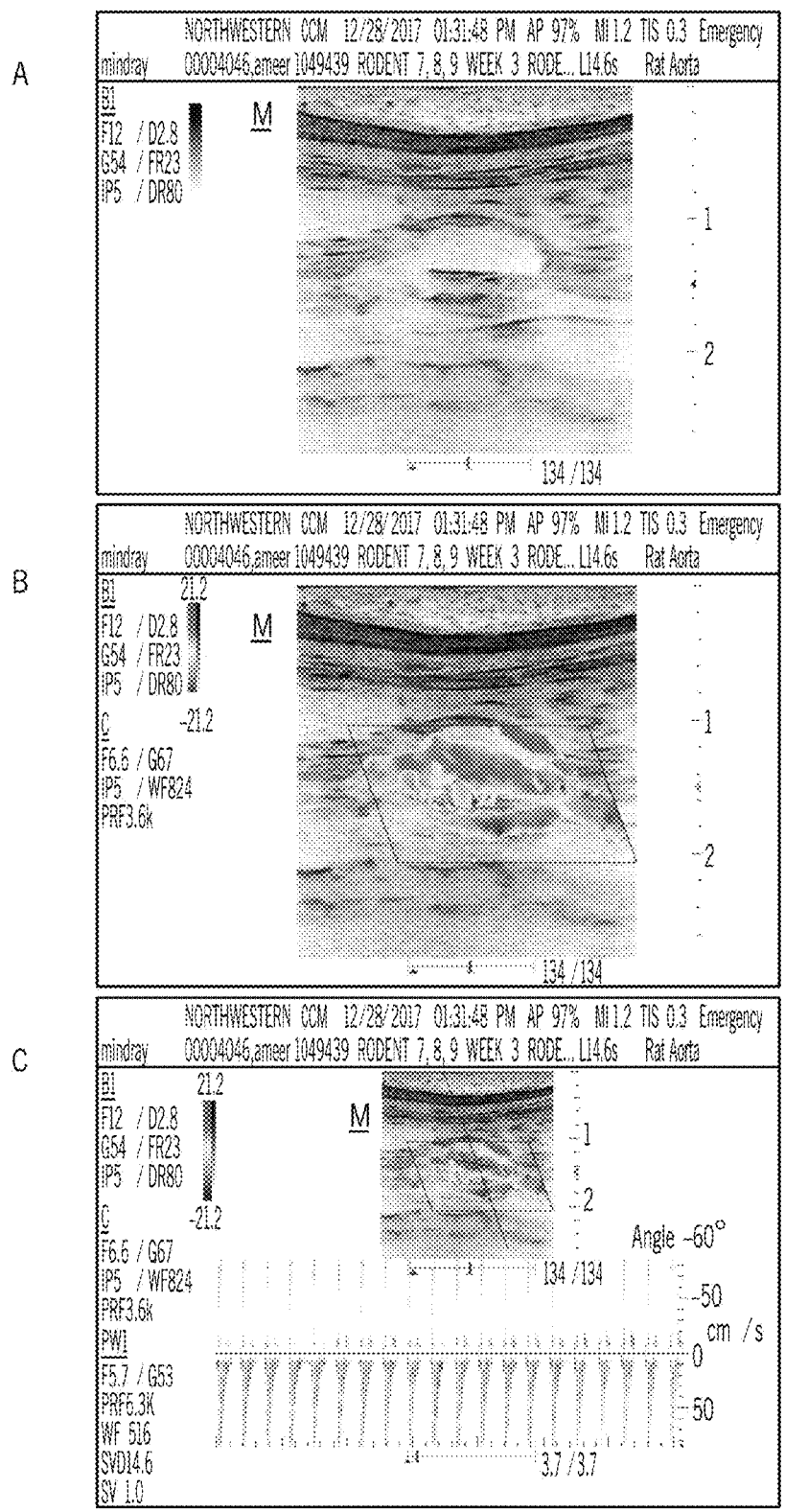
FIG. 36A-C. Ultrasound images of the same TG3 rat at the week 3 ultrasound time point now. (A) B Mode ultrasound image. (B) Color Mode ultrasound image. (C) Power Mode ultrasound image.

In some embodiments, the devices and systems herein find use in arteriovenous graft (AVG) placement for hemodialysis treatment as a strategy for Intravascular Retrievable Cell Delivery System for Islet Transplantation implant placement (FIG. 36) (Berardinelli, L. (2006). Grafts and Graft Materials as Vascular Substitutes for Haemodialysis Access Construction. European Journal of Vascular and Endovascular Surgery, 32(2), 203-211.; Rosas et al. (2003). Determinants of successful synthetic hemodialysis vascular access graft placement. Journal of Vascular Surgery, 37(5), 1036-1042.; herein incorporated by reference in its entirety). The AVG implantation approach has a number of strengths and weaknesses. The pros of using the AVG placement strategy for the devices and systems herein is it is a well-known surgical technique, AVGs for hemodialysis can be implanted into a variety of locations in the human body including the forearm, upper arm, or thigh, placement of the implant in the peripheral cardiovascular system is less invasive than placement in the central cardiovascular system, blood flow velocity in the suggested implant locations is fast and pulsatile, the implant location makes the device easily retrievable, there are multiple AVG implant locations and strategies, and it would not disrupt a vital body process (FIG. 36).

EXPERIMENTAL

Figure 2:
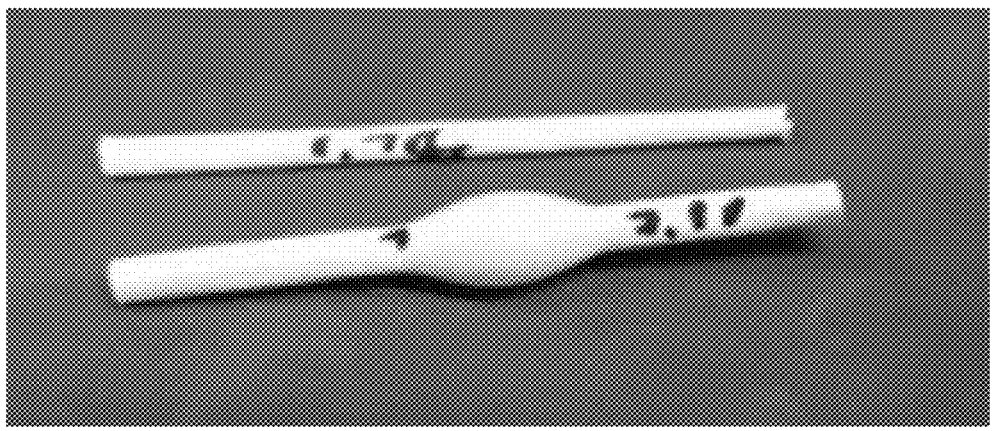
FIG. 2A-C. (A) An exemplary inner graft and outer graft. (B) The smaller diameter, inner vascular graft inserted into the lumen of the outer vascular graft. (C) The inner graft sitting flush on each end with the outer graft.
Figure 2:
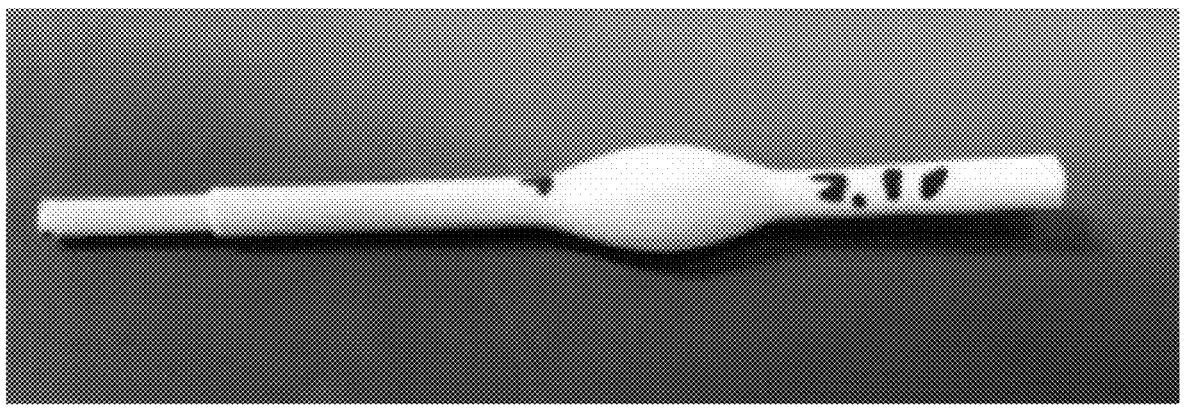
Figure 2:
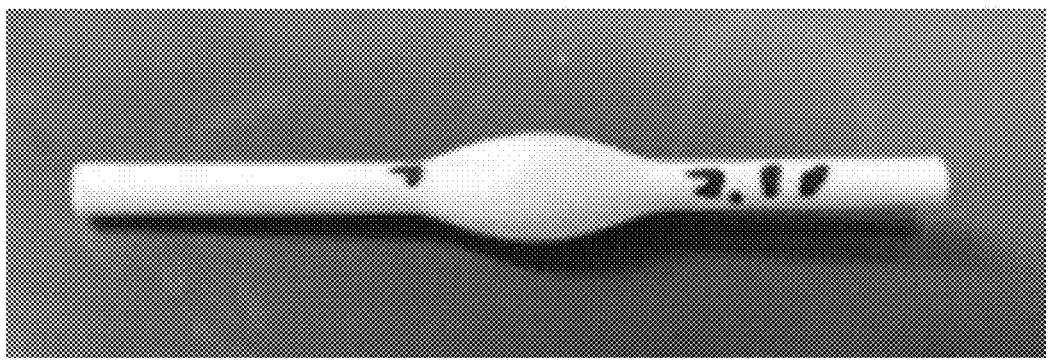

In an exemplary procedure for creation of the inflated midsection of the outer vascular graft, an Edwards Lifesciences Fogarty Arterial Embolectomy Catheter is inserted inside the lumen of the outer ePTFE vascular graft. The end of the balloon catheter is positions at the desired region of the expanded graft section. A syringe is attached to the end of the catheter containing 1 mL of air volume inside of the syringe (other volumes of air to create different sizes and geometries of the expanded portion of the vascular graft). Air is injected into the catheter and to inflate and permanently deform the graft. The syringe injection volume is held in place for ~1 minute to ensure permanent deformation of the graft. The syringe is then released causing deflation of the balloon catheter inside of the graft, allowing for its removal. An exemplary inner graft and outer graft expanded by the above procedure is depicted in FIG. 2A. Once the outer ePTFE vascular graft has an expanded midsection, the smaller diameter, inner vascular graft is inserted into the lumen of the outer vascular graft (FIG. 2B). In some embodiments, the inner graft will sit flush on each end with the outer graft when fully in place (FIG. 2C).

Figure 3:
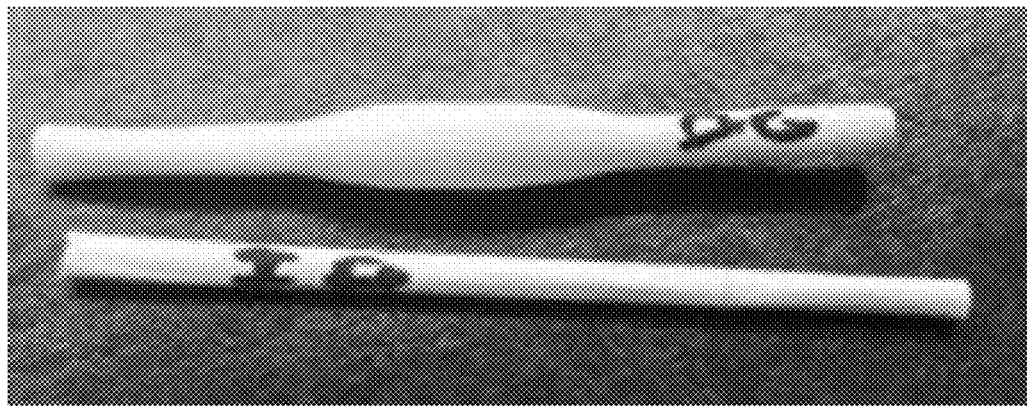
FIG. 3A-C. (A) an exemplary inner graft and outer graft with an extended deformation region, but smaller total diameter. (B) The inner vascular graft inserted into the lumen of the outer vascular graft. (C) The inner graft sitting flush on each end with the outer graft.
Figure 3:
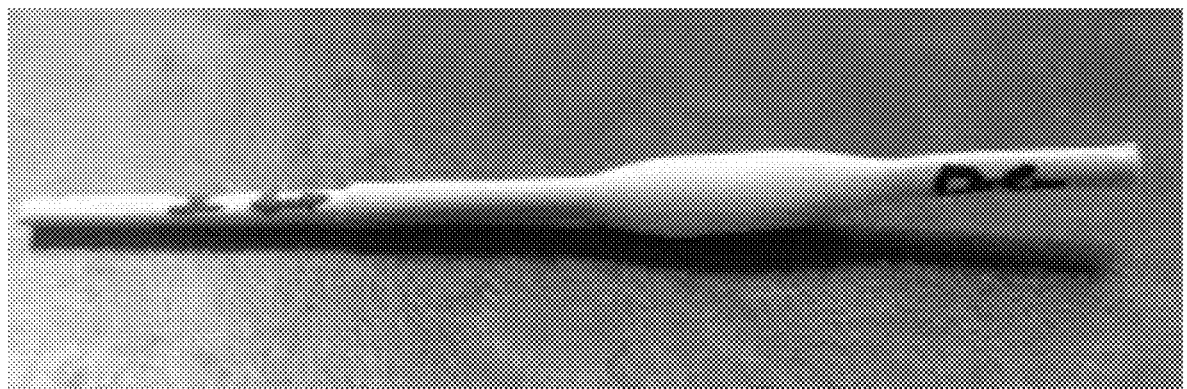
Figure 3:
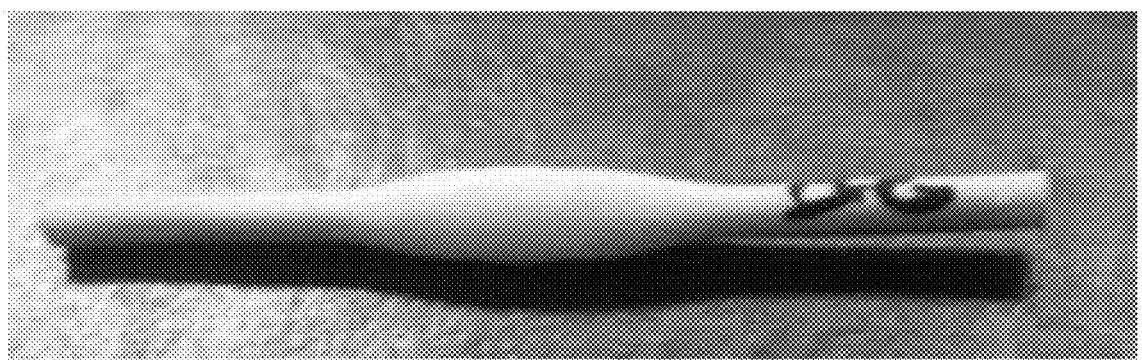
Figure 4:
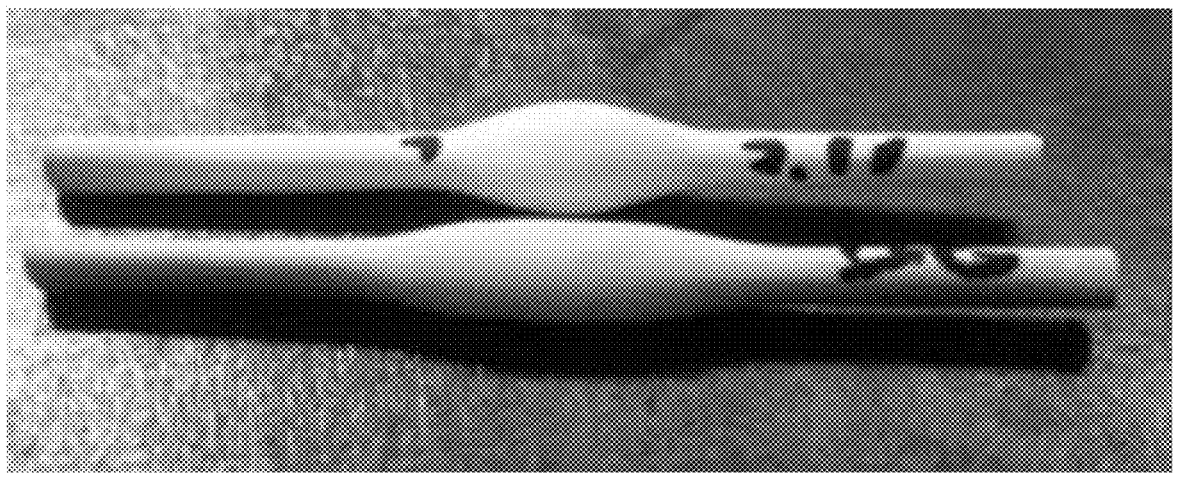
FIG. 4. Side-by-side comparison of the two exemplary devices depicted in FIGS. 2 and 3, respectively.
Figure 5:
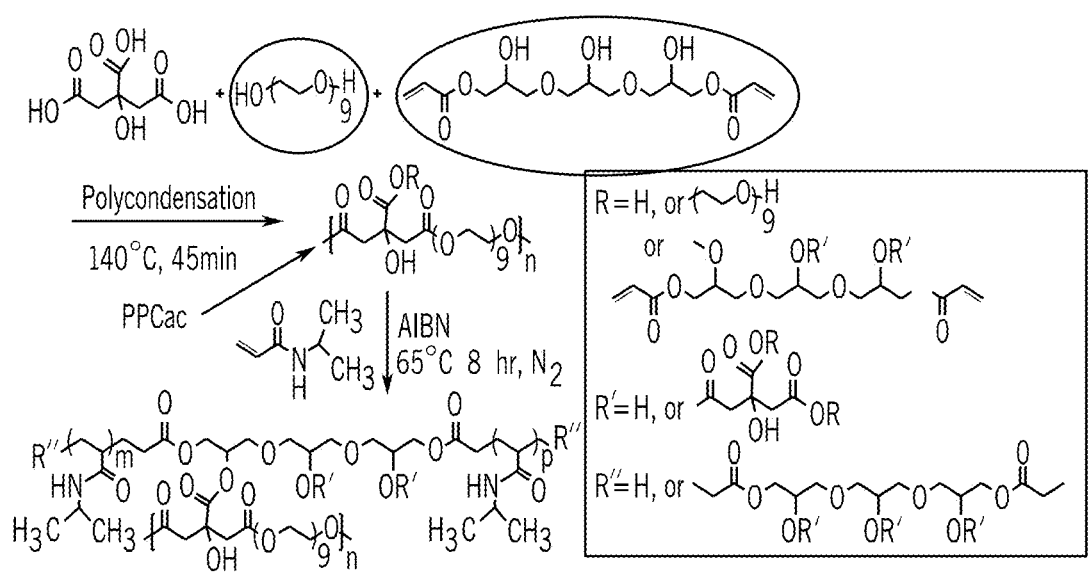
FIG. 5. Exemplary PPCN synthesis scheme.
Figure 6:
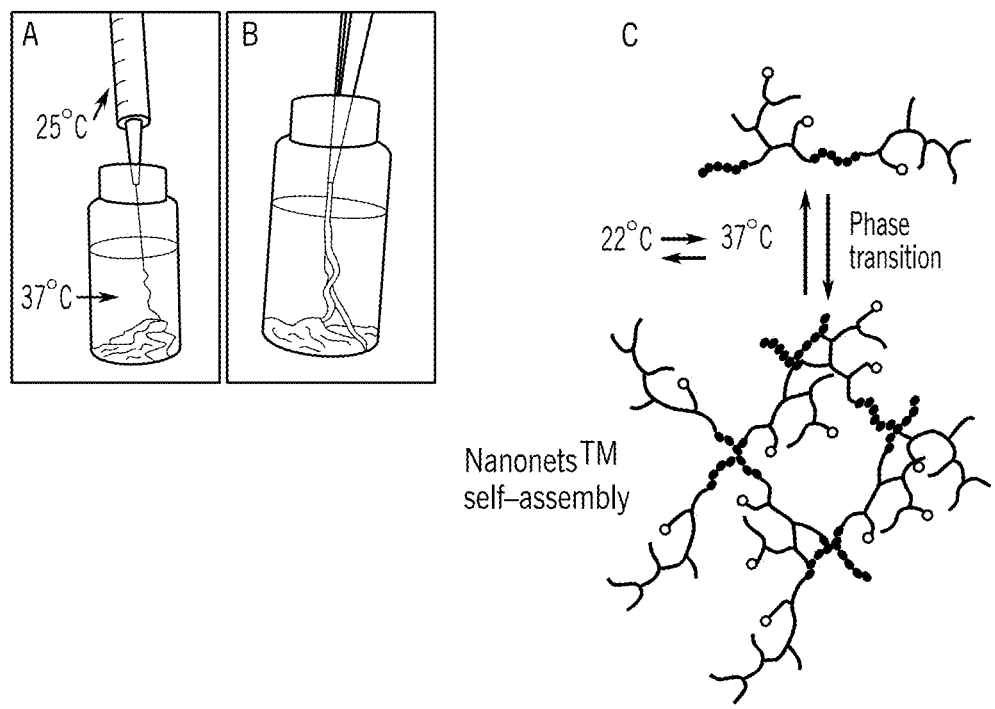
FIG. 6A-C. PPCN self-assembly. (A) Image depicting self-assembly upon phase transition. (B) Image depicting post-assembly PPCN. (C) Schematic of phase transition.
Figure 7:
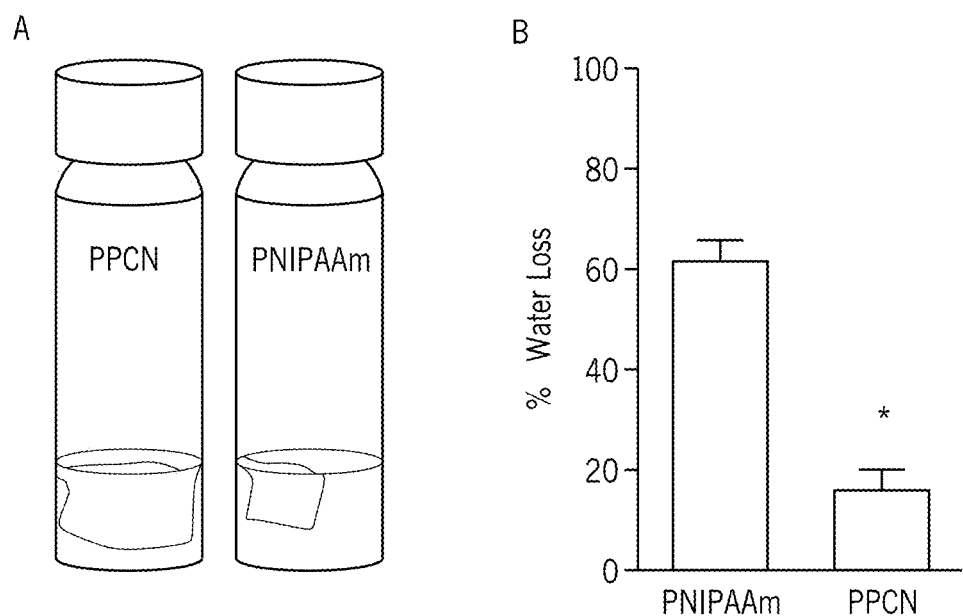
FIG. 7A-B. Comparison of PPCN and PNIPAAm. Image depicting PPCN and PNIPAAm in water. (B) Graph depicting % water loss of PPCN and PNIPAAm.
Figure 8:
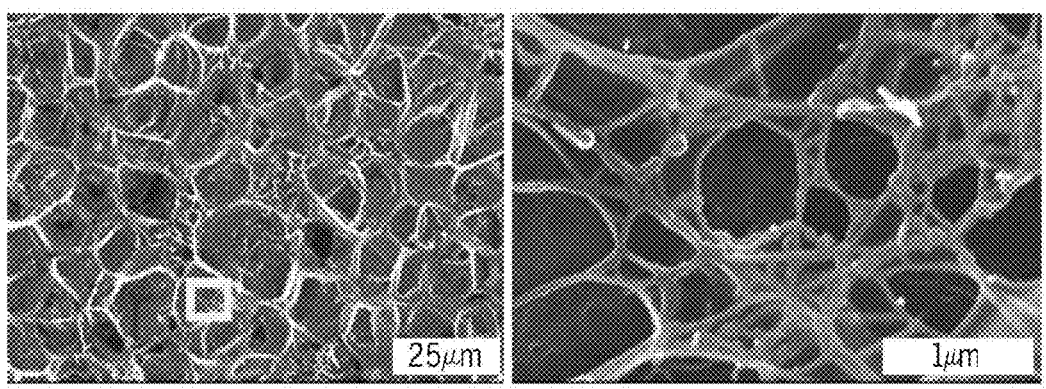
FIG. 8. Electron micrographs depicting hierarchical nano-microoscale features of PPCN.
Figure 9:
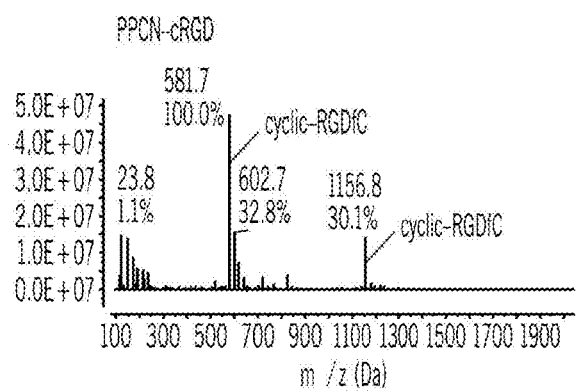
FIG. 9. Synthesis and Characterization of cRGD-PPCN MALDI spectrum of PPCN-cRGD (top left); major peaks include cyclic-RGDfC at 581.7 m/z and full monomer at 1156 m/z. PPCN vs PPCN-cRGD live-dead cell staining (top right). Imaging (bottom).
Figure 9:
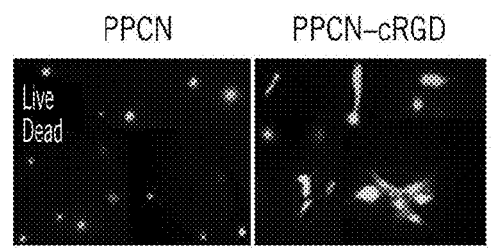
Figure 9:
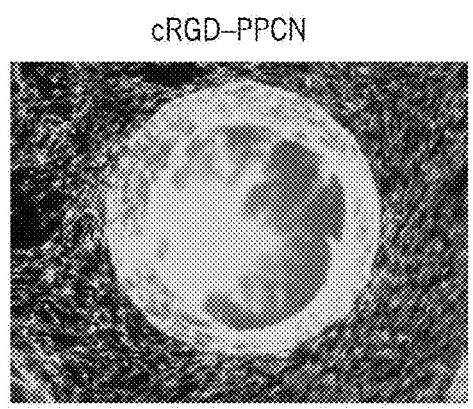
Figure 9:
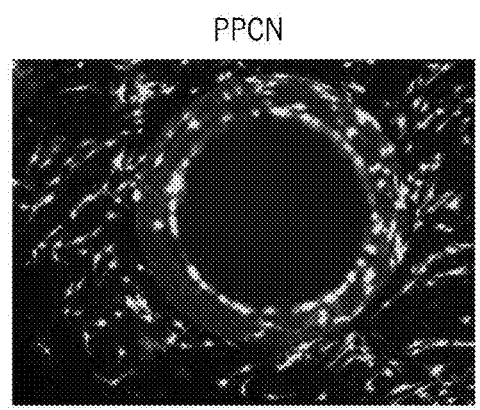
Figure 10:
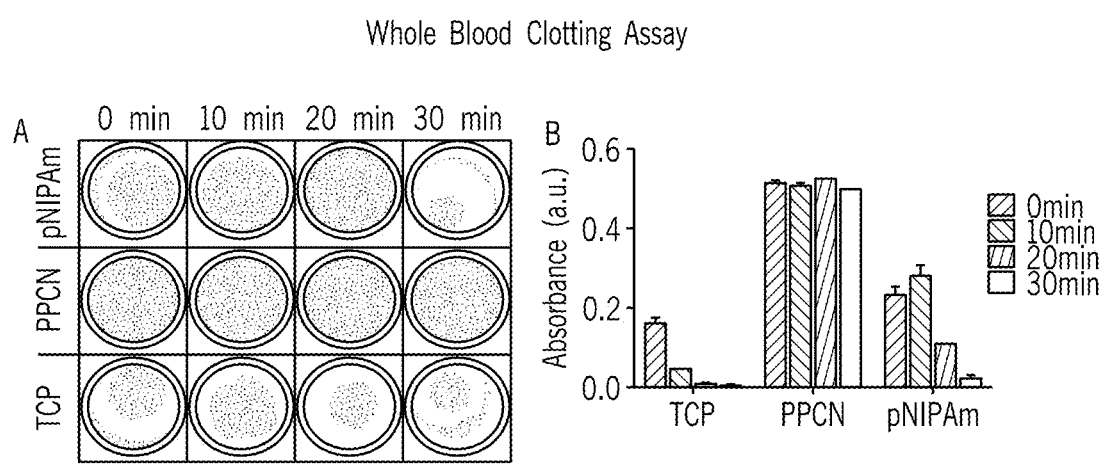
FIG. 10A-B. Whole blood clotting assay depicting the thromboresistant properties of PPCN. (A) Images. (B) Graph of absorbance.
Figure 11:
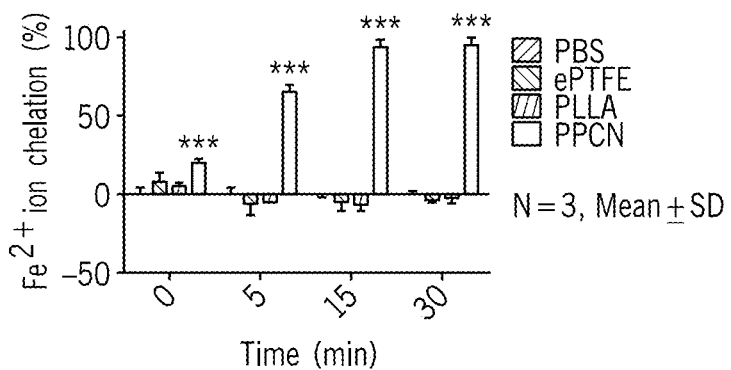
FIG. 11A-C. PPCN antioxidant properties. (A) Graph depicting $Fe^{2+}$ ion chelation. (B) Graphs depicting lipid peroxidation. (C) Graph depicting free radical scavenging.
Figure 11:
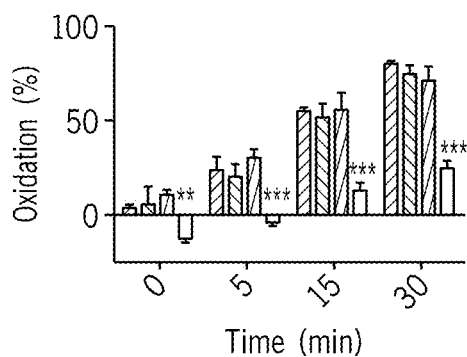
Figure 11:
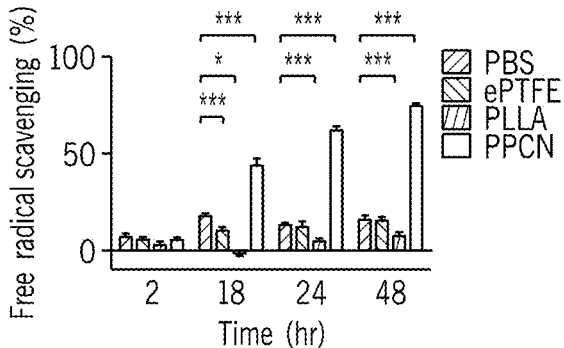
Figure 12:
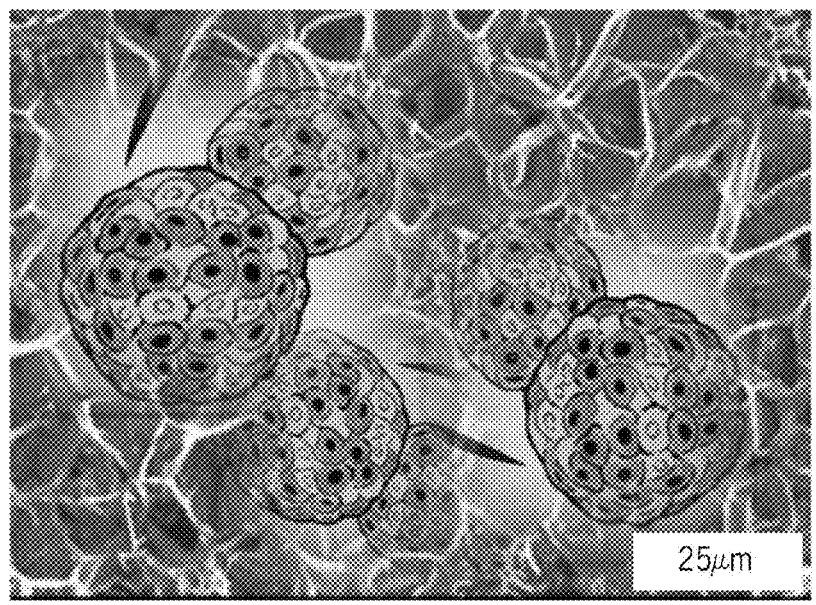
FIG. 12. Cartoon depicting a PPCN tailored environment for islet clusters.
Figure 13:
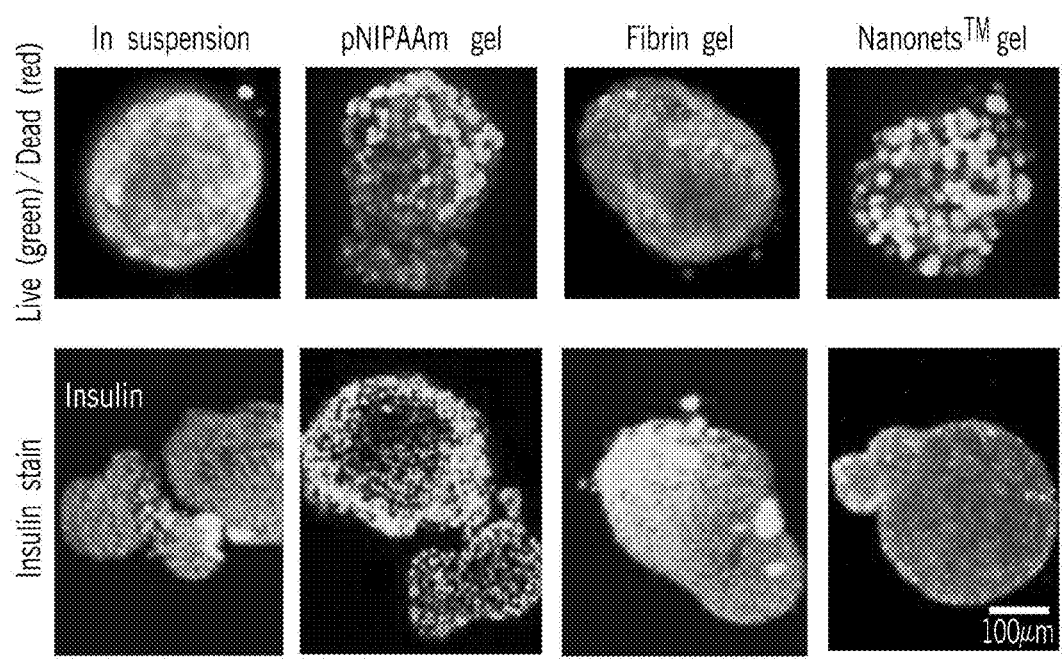
FIG. 13. Images depicting islet clusters in vitro.
Figure 14:
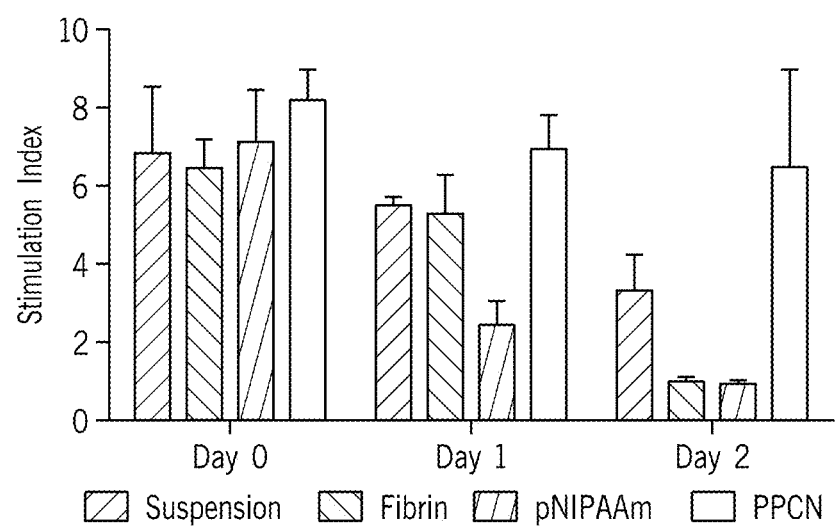
FIG. 14. Graph of islet function in vitro.
Figure 15:
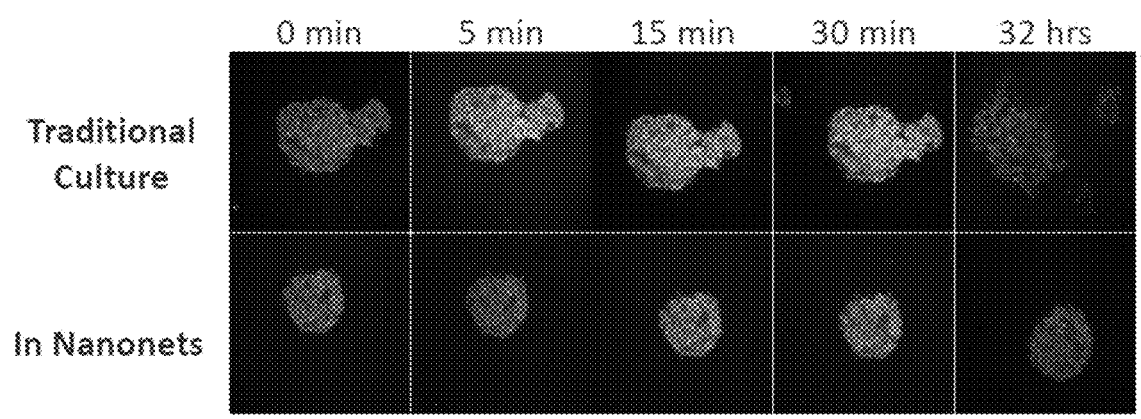
FIG. 15. Images depicting protection of islets from oxidative damage by PPCN.
Figure 16:
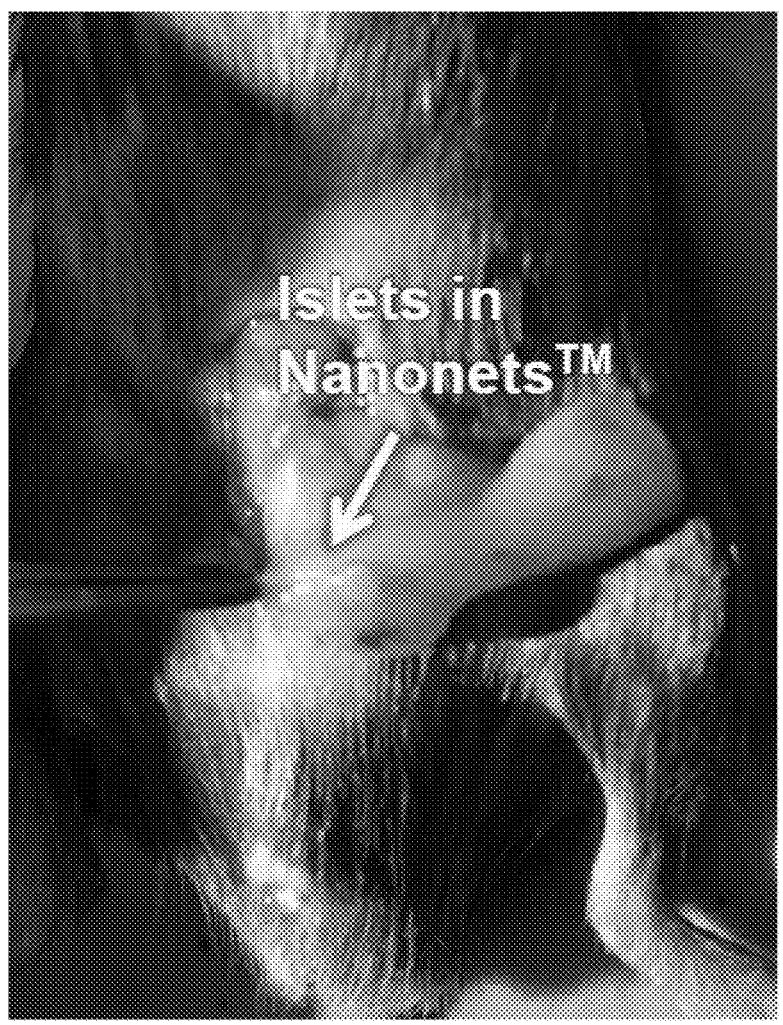
FIG. 16. Image depicting implantation of islets in PPCN into a mammalian subject.
Figure 17:
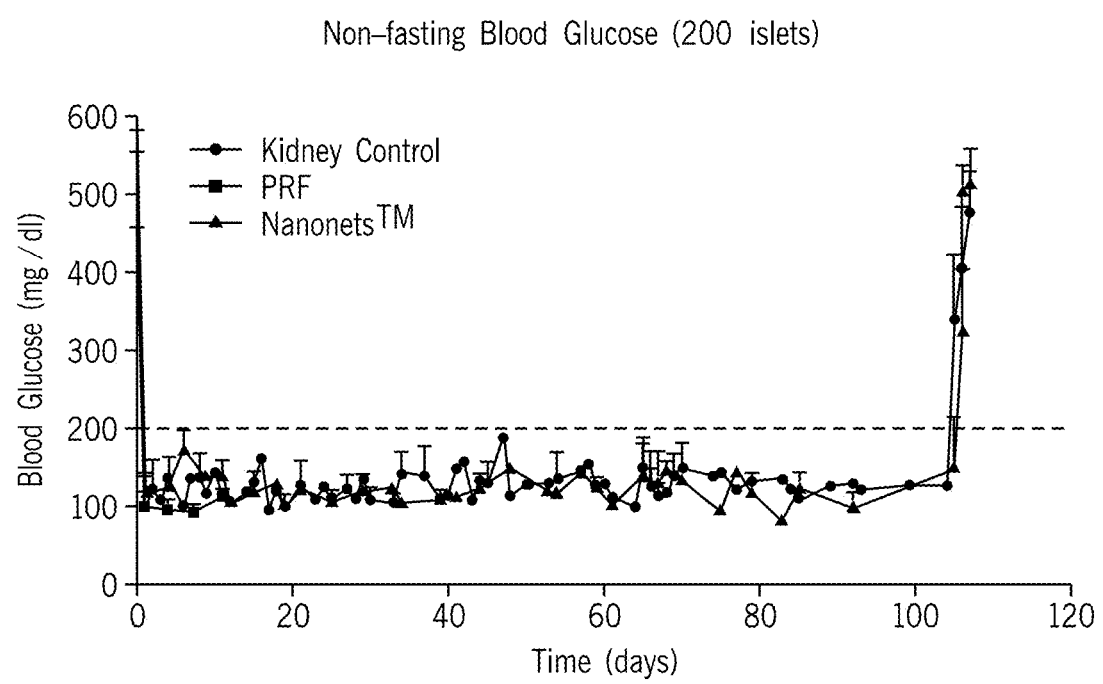
FIG. 17. Graph depicting non-fasting blood glucose after islet transplantation (200 islets).
Figure 18:
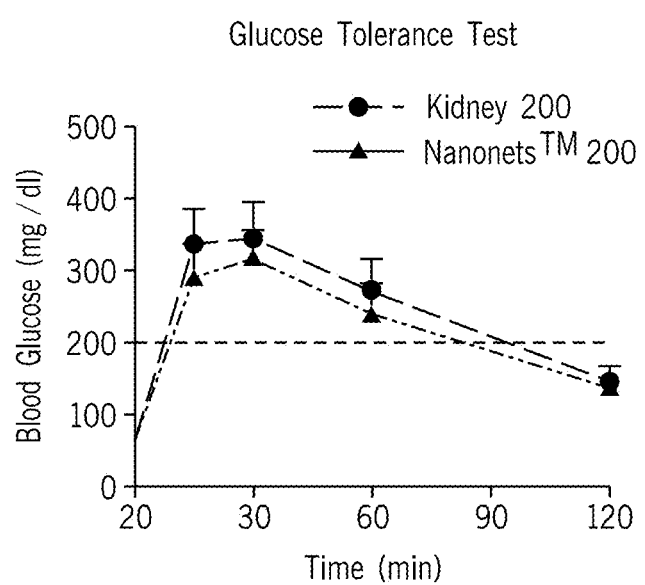
FIG. 18. Graph depicting results of a glucose tolerance test following extrahepatic islet transplantation (200 islets).
Figure 19:
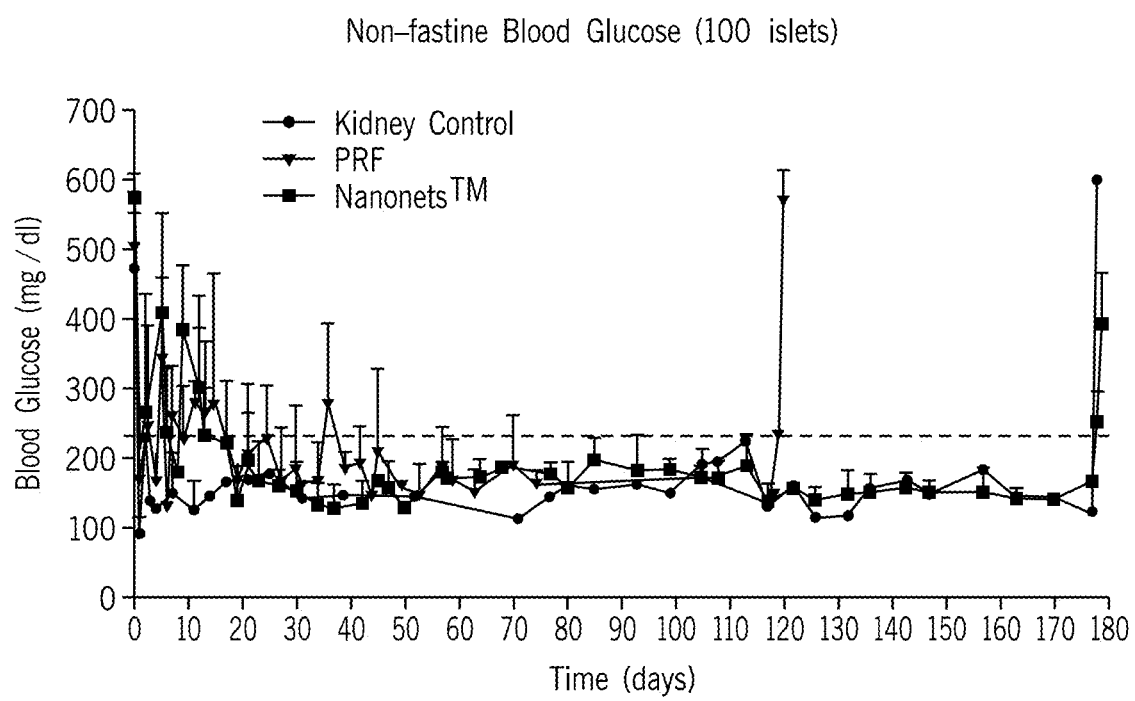
FIG. 19. Graph depicting non-fasting blood glucose after islet transplantation (100 islets).
Figure 20:
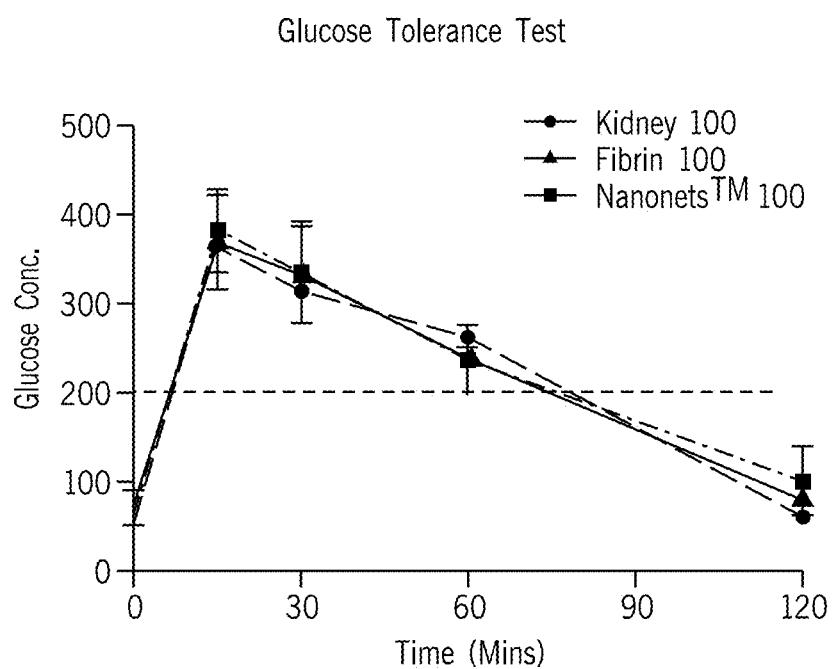
FIG. 20. Graph depicting results of a glucose tolerance test following extrahepatic islet transplantation (100 islets).
Figure 21:
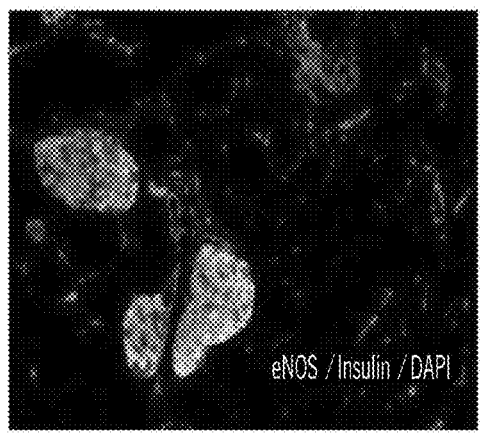
FIG. 21. Extrahepatic Islet Transplantation
Figure 21:
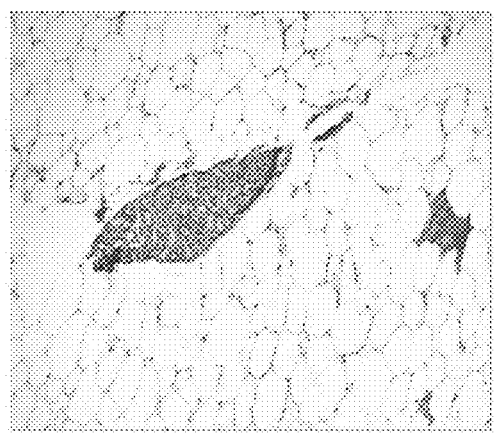

Using alternative inflation parameters, but the same general procedure, alternative geometries of the expanded section are achievable. FIG. 3A-C depicts an exemplary device created using 0.7 mL of air, and the balloon catheter was inflated at three points in the outer vascular graft to produce a longer deformation in length, but smaller in total diameter.

Figure 22:
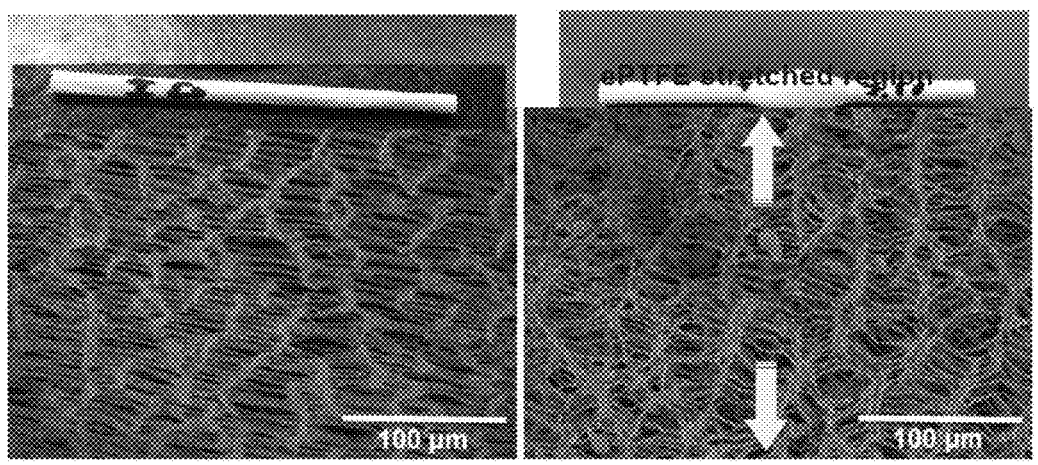
FIG. 22. Electron micrographs of an undeformed versus a deformed vascular graft.
Figure 23:
FIG. 23A-D. MicroCT images demonstrating the hydrogel within the compartment that was created in the ePTFE tube.
Figure 23:
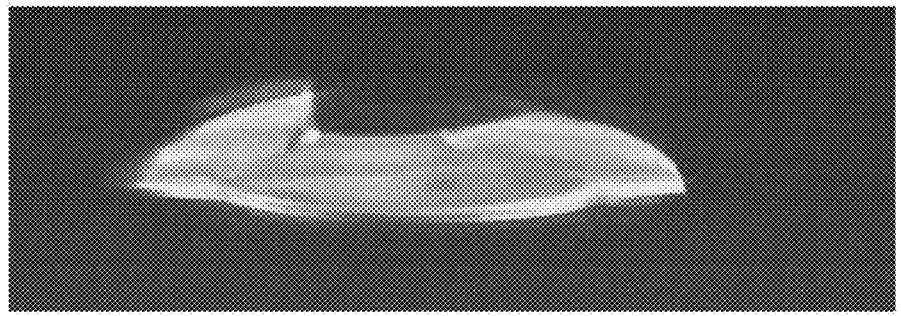
Figure 23:
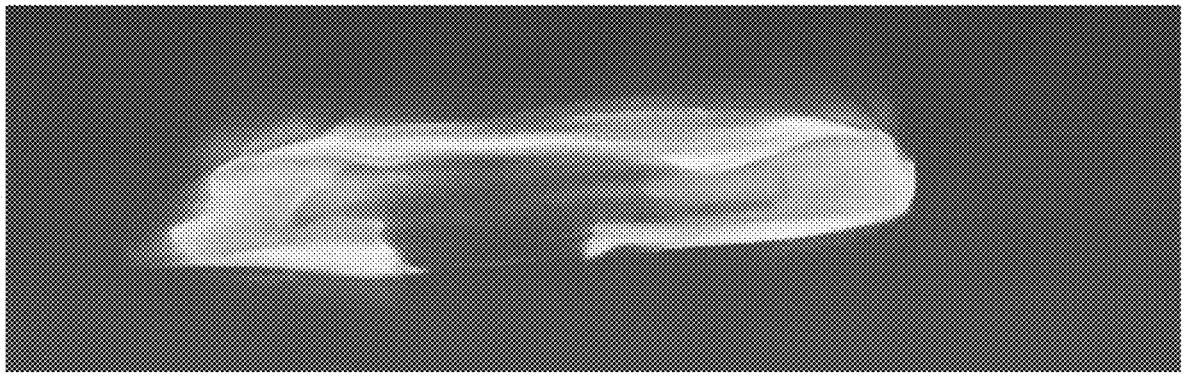
Figure 23:
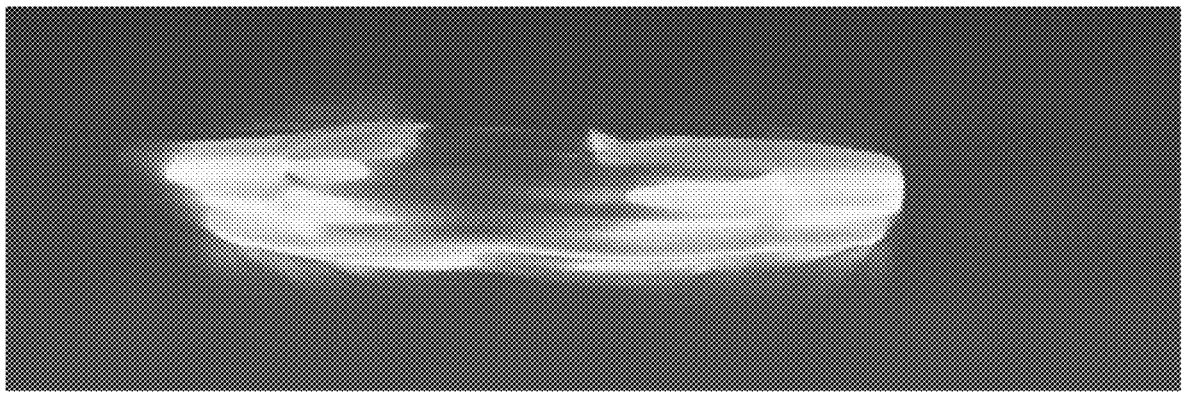

A variety of different shaped and sized devices have been produced using the methods described herein (FIGS. 22 and 23).

Figure 24:
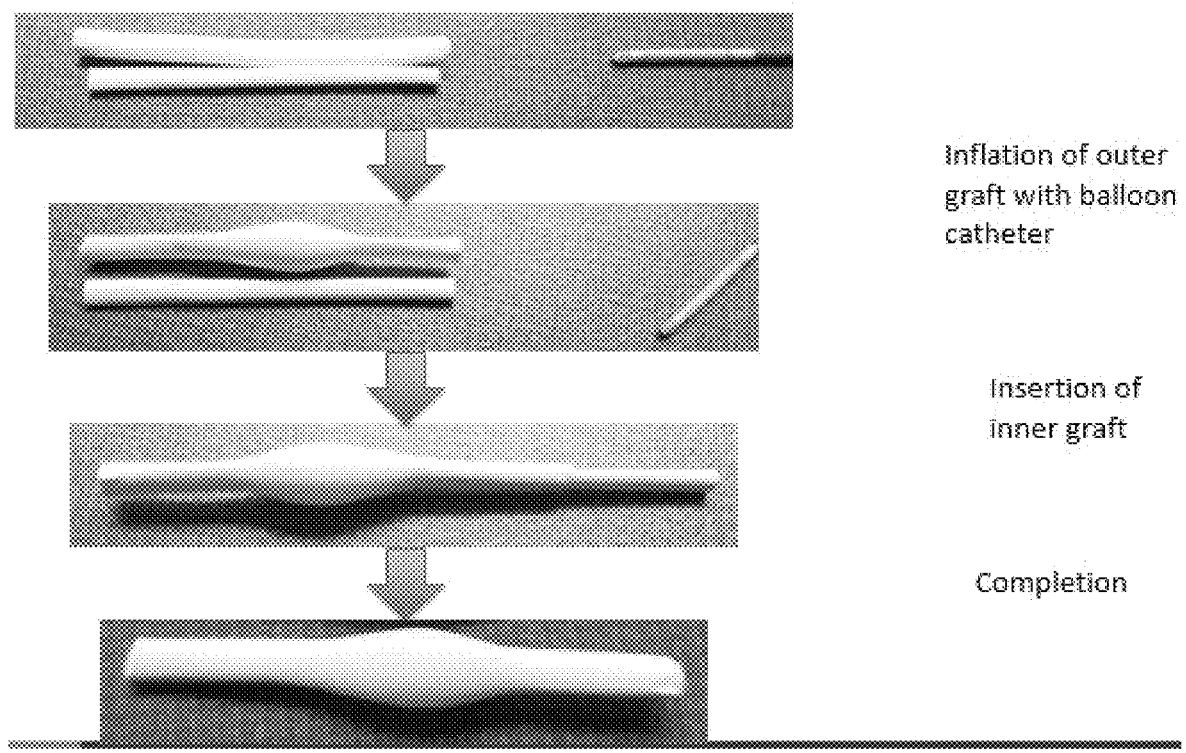
FIG. 24. Images depicting the process of making an exemplary intravascular retrievable cell delivery system for islet transplantation with two ePTFE vascular grafts.

The dual vascular graft design for the intravascular cell delivery system for islet transplantation was modeled and evolved extensively in Solidworks CAD software (FIG. 24).

Figure 25:
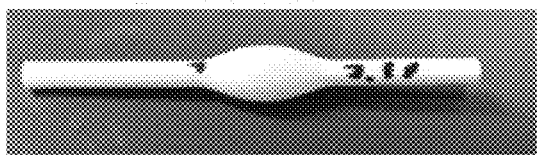
FIG. 25. Images depicting rat-sized devices made using the dual graft creation method of making the intravascular retrievable cell delivery systems for islet transplantation.
Figure 25:
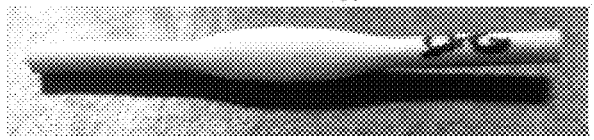
Figure 25:
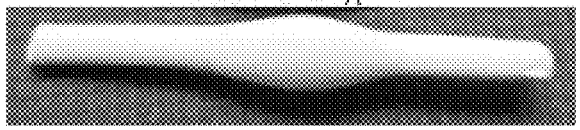
Figure 25:
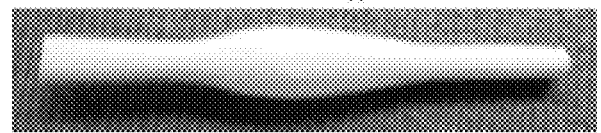
Figure 25:

Additional analysis of the intravascular retrievable cell delivery systems was performed including refining the SEM images of the microstructure of the vascular grafts that were deformed by a balloon catheter (FIG. 25).

Figure 26:
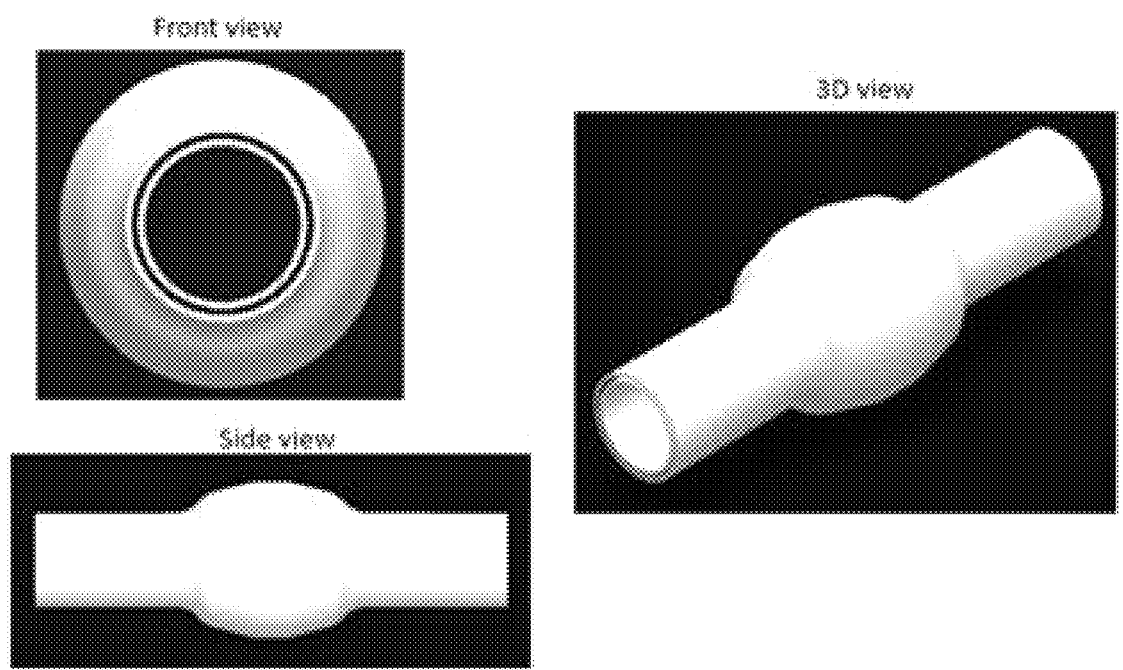
FIG. 26. Exemplary design of an intravascular retrievable cell delivery system containing an inner vascular graft and a deformed outer vascular graft.
Figure 28:
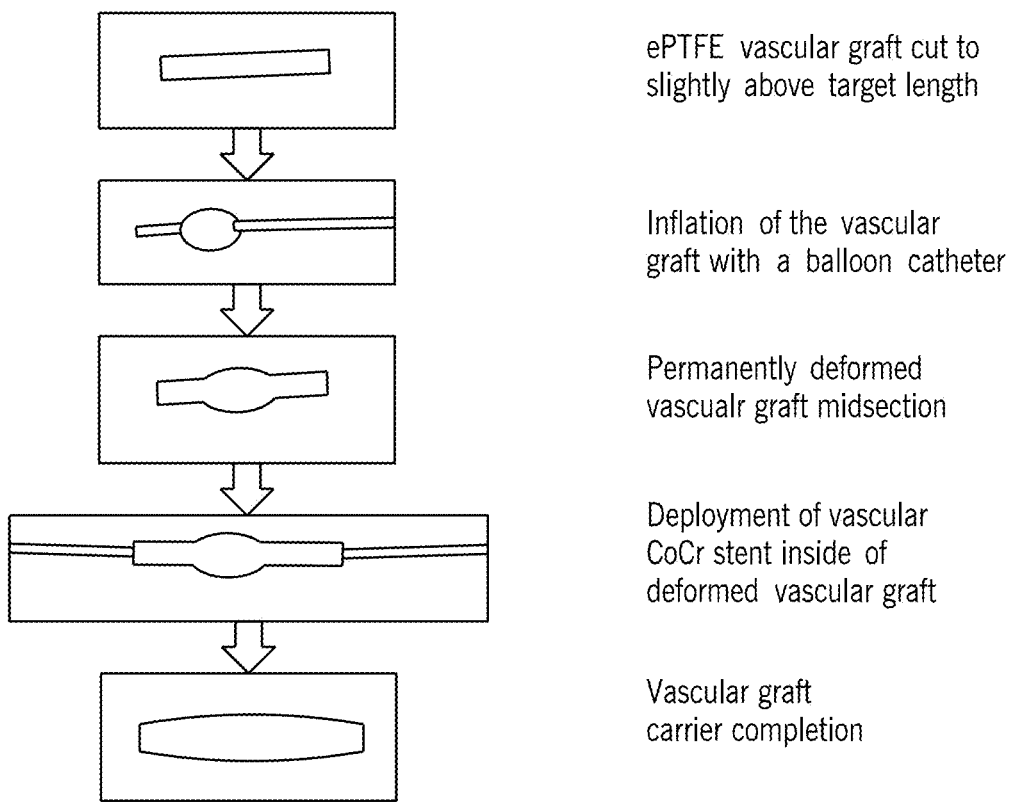
FIG. 28. An exemplary process of making the devices and systems herein with a vascular stent deployed inside of the deformed vascular graft midsection, replacing the undeformed graft to create the concentric space for delivering islets, hydrogels, drugs, etc. to the vascular system.
Figure 29:
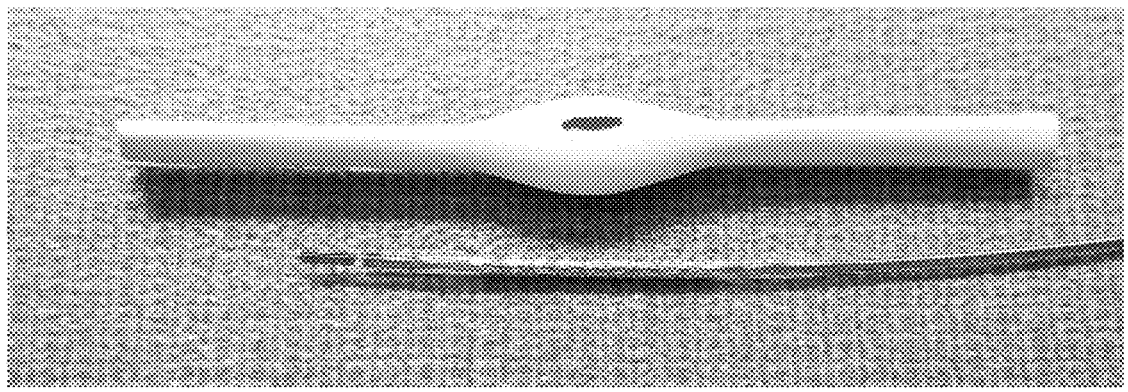
FIG. 29. Before (top) and after (bottom) images of a vascular stent deployed inside of a deformed vascular graft's midsection.
Figure 29:
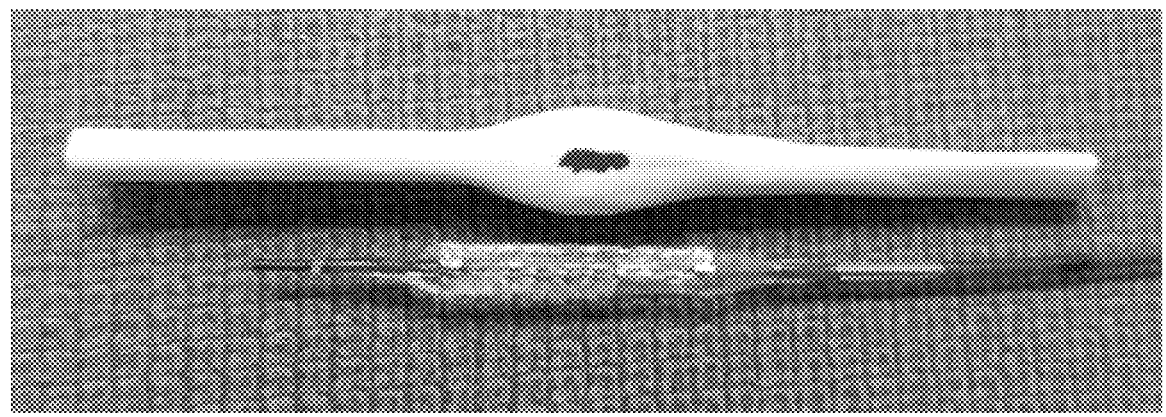

Experiments were conducted during development of embodiments herein to develop an alternative methodology for creating the devices and systems described herein. In the alternative method, instead of inserting an undeformed inner vascular graft into a deformed vascular graft (dual vascular graft), a vascular stent is deployed into the deformed midsection of the outer vascular graft (stented vascular graft) (FIG. 26). In some embodiments, this process provides the outer deformed vascular graft with a more stable and permanent deformation of the graft lumen while also preventing the graft deformation from collapsing. The concentric midsection of the device is in between the inner vascular graft wall and the deployed vascular stent within the deformation. This region of the device is used to store and transplant islets, PPCN, and/or other cell types, hydrogels, drugs, and/or other deliverables. Additionally, these stents have a higher degree of permeability than the inner vascular graft, and allow for more blood metabolites and glucose to diffuse to the islets housed in the concentric midsection, and in return allow islets to easily diffuse insulin and waste products into the blood. FIG. 26 details the alternative process of making the devices and systems herein using the stenting of the vascular graft deformation methodology. The stented vascular graft design for the intravascular cell delivery system for islet transplantation was also modeled and evolved extensively in Solidworks (FIG. 29).

Experiments were conducted during development of embodiments herein to perform in vivo testing if systems and devices herein in Sprague-Dawley Rats using the Rat Abdominal Aorta Interposition Model. This study tested the feasibility and efficacy of using the systems and devices herein for delivery of islets in a living organism. Moreover, the ability of the vascular implant to not impede or detrimentally alter blood flow was established as well. For this purpose, Sprague-Dawley Rat Abdominal Aorta Interposition Models were divided into 3 Testing Groups (TGs) were N=3 rats were used for each group (Table 1). Systems for this study were made using the procedure described in FIG. 26.

TABLE 1

The 3 Testing Groups (TGs) of the in vivo rat study.

|  | TG1 | TG2 | TG3 |
| --- | --- | --- | --- |
| ePTFE Vascular Graft | Yes | Yes | Yes |
| CoCr Stent | Yes | Yes | Yes |
| Deformed Graft Midsection | No | Yes | Yes |
| Injection PPCN into Graft Midsection | No | No | Yes |

Figure 30:
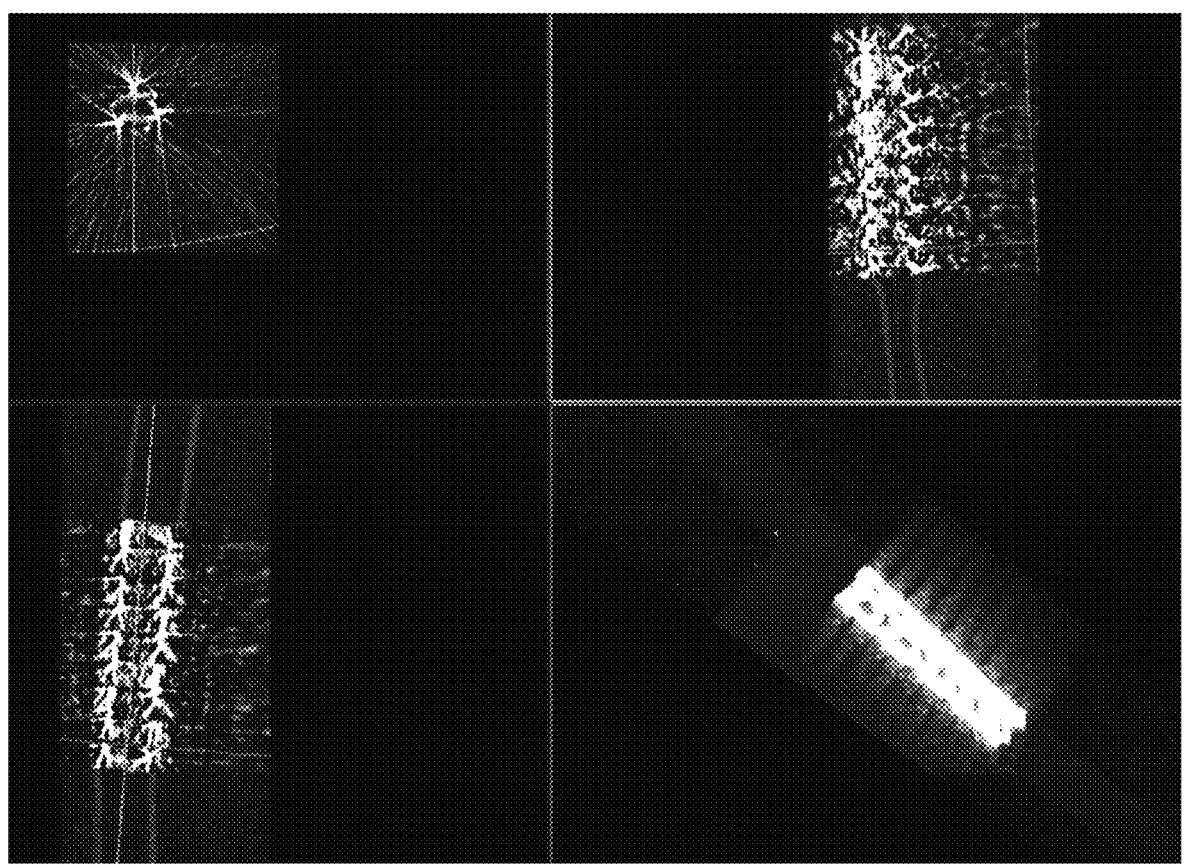
FIG. 30. A microCT images of the system depicted in FIG. 29, demonstrating successful deployment of the vascular stent inside of the deformed vascular graft.

The outer vascular graft is a 1.5 mm inner diameter Aeos ePTFE Extruded Sub-Lite-Wall Vascular Graft produced by Zeus Inc. The vascular graft was inflated and deformed by a 2 French Fogarty Arterial Embolectomy Catheter produced by Edwards Lifesciences. The stent deployed inside of the deformed graft's midsection is the 2 mm diameter by 8 mm length Multi-Link Mini Vision Cobalt Chromium Coronary Stent produced by Abbott Vascular. A larger diameter vascular stent was used to create an interference fit with the smaller diameter ePTFE vascular graft to ensure that the stent does not move around or become displaced when subjected to arterial blood flow. This system is exemplary, and for testing purposes, systems are not so limited. A wide variety and combination of different sized vascular grafts, vascular stents, and balloon catheters find use in the creation of different deformation geometries and sized vascular graft carriers. Calculations on the volume of material the concentric midsection of the TG3 vascular grafts can hold are shown in FIG. 30.

The typical number of islets transplanted into diabetic rats for islet transplantation surgery is 4,000 islets per animal (Omer et al. (2004). Exercise Induces Hypoglycemia in Rats With Islet Transplantation. Diabetes, 53(2), 360-365.; herein incorporated by reference in its entirety). The systems herein are capable of meeting and/or exceeding the volume requirements needed for rat islet transplantation and are able to fit additional materials into the graft, such as PPCN without compromising the integrity of the vascular implant.

Figure 31:
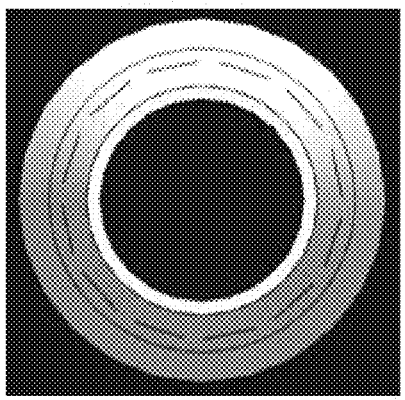
FIG. 31. A SOLIDWORKS model representing a stent deployed inside of the deformed midsection of a vascular graft.
Figure 31:
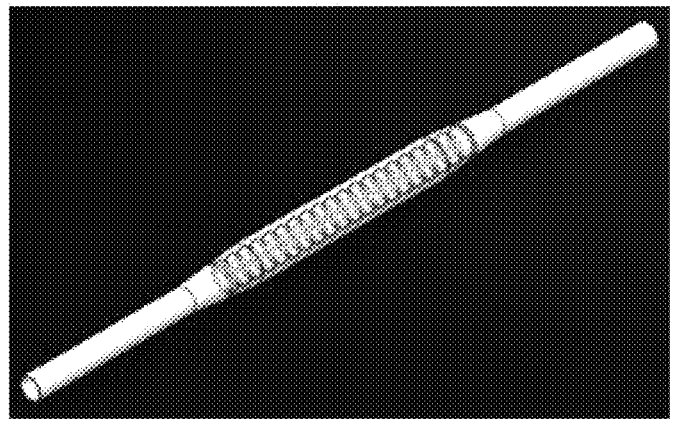
Figure 31:
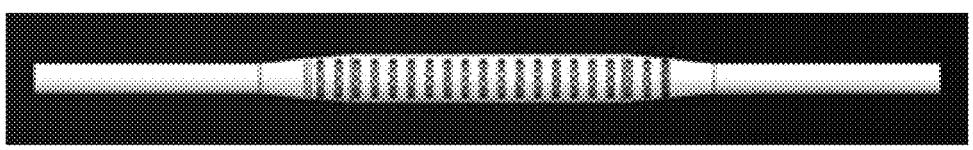

An in vivo study timeline was established in conjugation with the Northwestern Microsurgery core (FIG. 31). The study began with an Abdominal Aortic Interposition Surgery with the implantation of the Intravascular Retrievable Cell Delivery System for Islet Transplantation into each rodent performed by the Northwestern Microsurgery Core in Chicago, Ill. The aortic interposition surgery was followed by three Doppler ultrasound readings at weeks 1, 2, and 3 respectively in order to access the functionality of the vascular implant in vivo, to check for any disturbances or blockages of the vascular graft lumen, analyze blood flow properties through the vascular graft, and to record the peak systolic blood velocity within the Intravascular Retrievable Cell Delivery System for Islet Transplantation within the animal at each time point, and analyze if any of these properties or values changed significantly throughout the duration of the study. Euthanasia of the rat and collection of both the native aorta and vascular implant was collected at the study endpoint exactly 4 weeks (28 days) after the Intravascular Retrievable Cell Delivery System for Islet Transplantation was surgically implanted. Rat Surgery photos are shown in FIG. 32, demonstrating the ability of the Intravascular Retrievable Cell Delivery System for Islet Transplantation to be successfully implanted into a rodent's cardiovascular system following the Abdominal Aorta Interposition Model.

Figure 34:
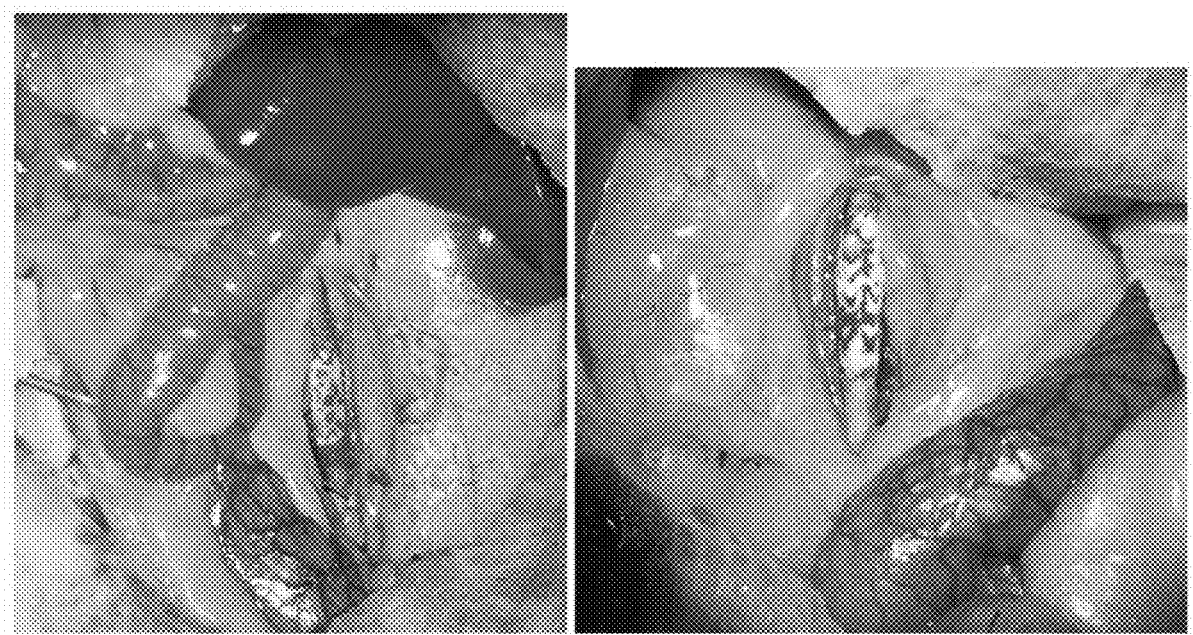
FIG. 34. Abdominal aorta interposition surgery with a vascular implant from TG1 (left) and a vascular implant from TG2 (right) with an inflated midsection. The Intravascular Retrievable Cell Delivery Systems for Islet Transplantation are white with blood spots and are fully attached to the proximal and distal native rat aorta. Photos were taken immediately following anastomosis and reperfusion of the vascular graft.
Figure 35:
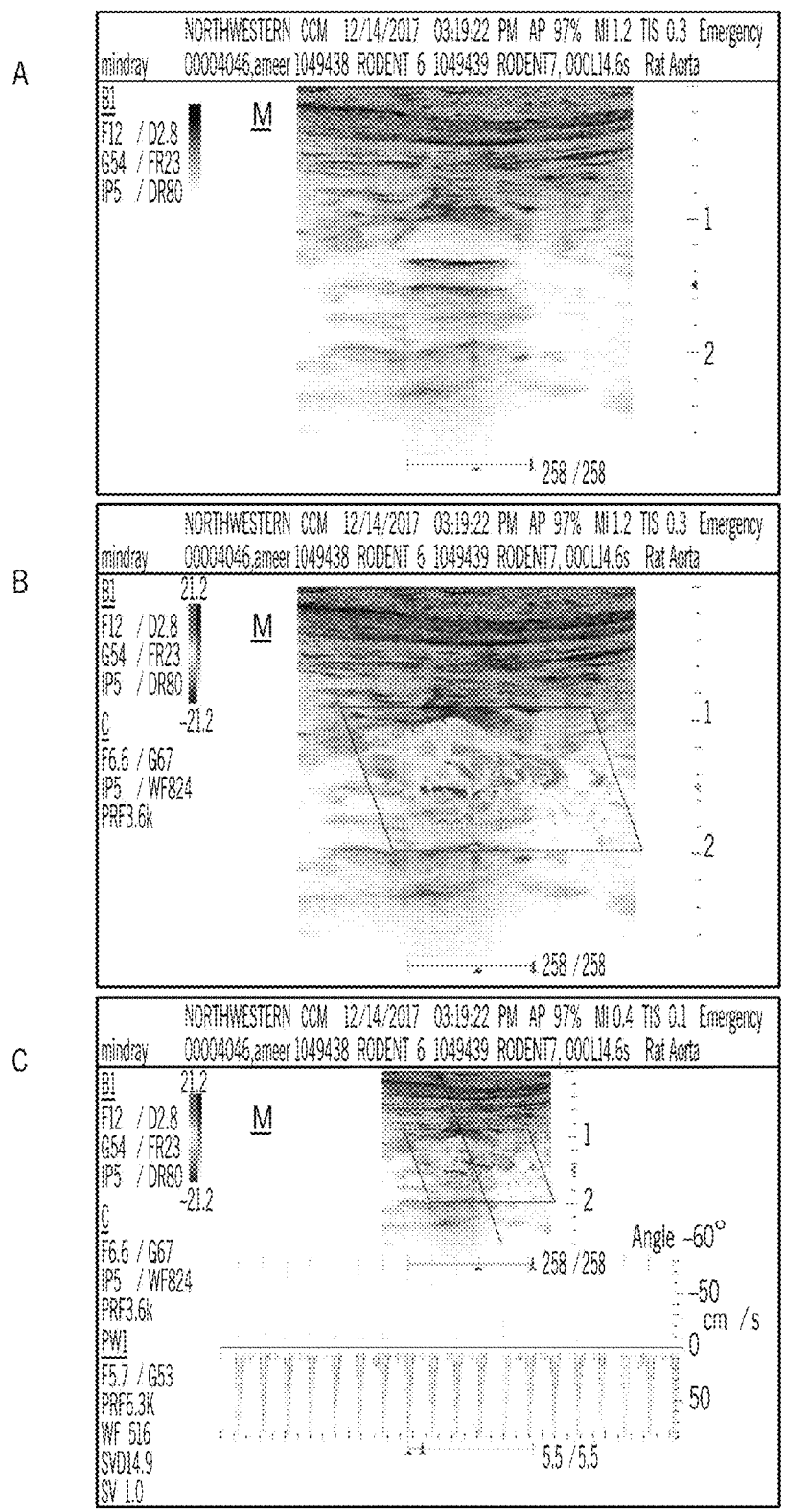
FIG. 35A-C. Ultrasound images of a TG3 rat at the week 1 ultrasound time point. (A) B Mode ultrasound image. (B) Color Mode ultrasound image. (C) Power Mode ultrasound image.

Ultrasound imaging was performed at the week 1, 2, and 3 time points. The ultrasound machine used was the Mindray M7 Portable Ultrasound Machine. Ultrasound imaging modalities used were B-Mode, Color Mode, and Power Mode (FIGS. 33 and 34). The rat abdominal aortic peak systolic velocity was recorded during each of the ultrasound checks at the concentric midsection of the Intravascular Retrievable Cell Delivery (FIG. 35). FIG. 35 shows the week 1 ultrasound images from a TG3 rat while FIG. 34 shows the week 3 ultrasound images of the same TG3 rat for comparison.

The process of making the stented vascular grafts herein is repeatable for a wide variety of different shaped and sized vascular grafts, vascular stents, and balloon catheters. Experiments conducted during development of embodiments herein included rat sized vascular implants 1.5 mm in inner diameter up through 8 mm inner diameter vascular grafts intended for use in humans.

Figure 37:
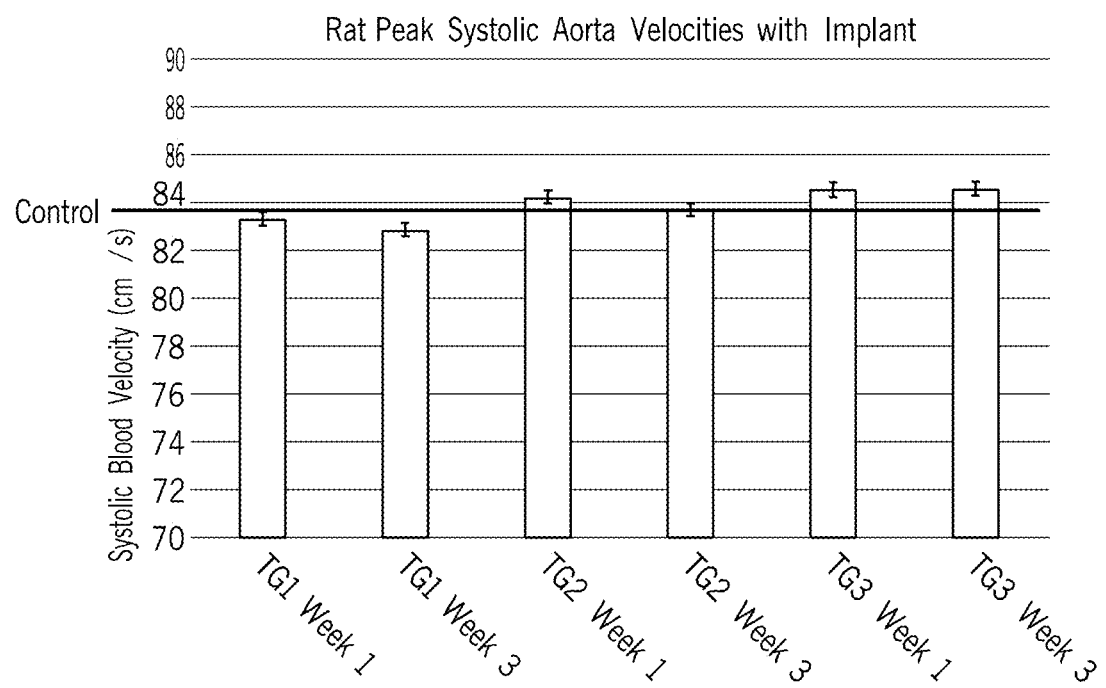
FIG. 37. Week 1 vs. Week 3 rat aortic peak systolic blood velocity measurements taken using the Power Mode setting on the Mindray M7 Portable Ultrasound Machine. The control rat aortic velocity measurements were taken in the same rats that were going to be used in the implantation study 2 weeks before they received their Intravascular Retrievable Cell Delivery System for Islet Transplantation aortic interposition surgery.
Figure 38:
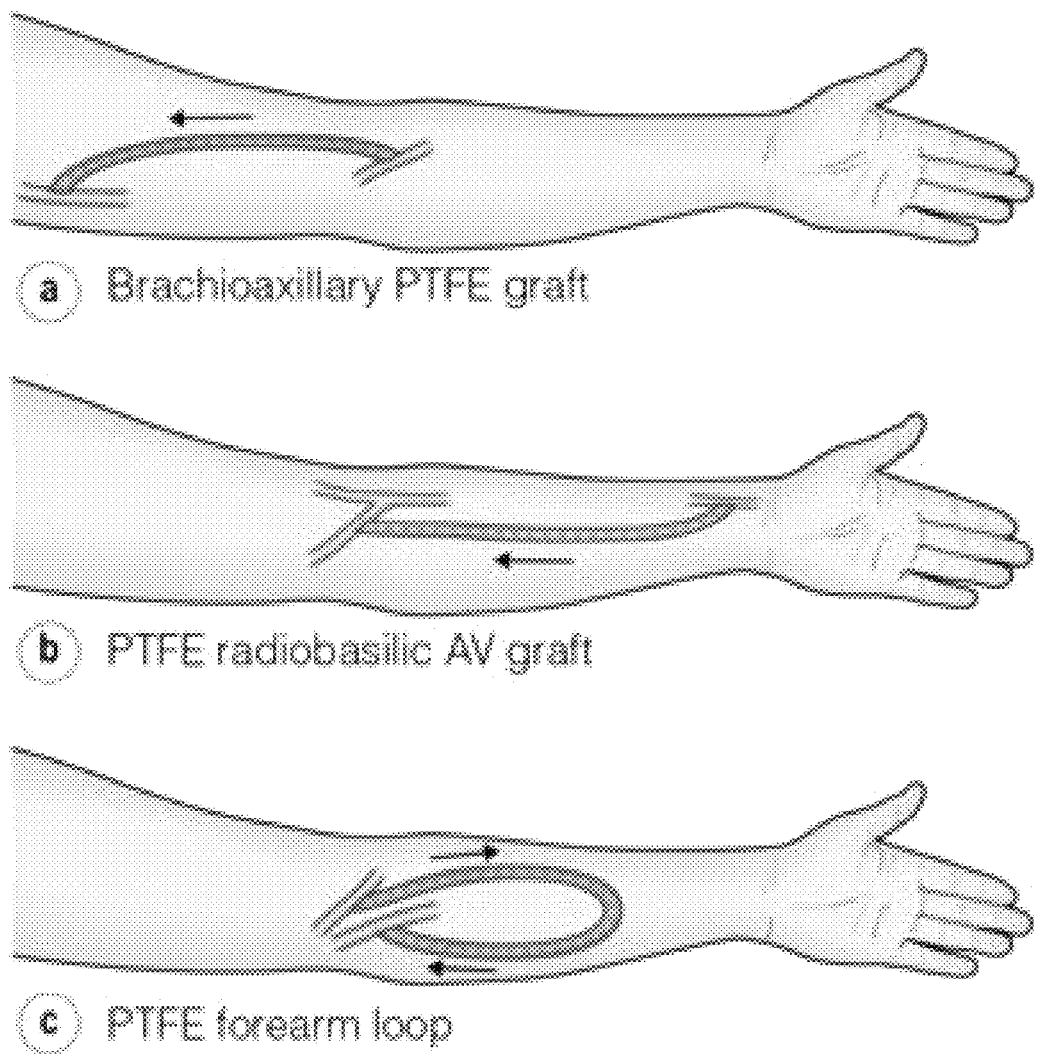
FIG. 38. Three implantation locations of the systems and devices herein. Other implantation locations throughout a patient's arm or thigh are possible using the AVG implantation approach.

Exemplary 'human-sized' systems and devices were created using a 6 mm inner diameter Impra ePTFE Thinwall Vascular Graft produced by Bard Peripheral Vascular, an 8 mm diameter 59 mm length Omnilink Elite Vascular Balloon-Expandable Cobalt Chromium Stent produced by Abbott Vascular was deployed within the vascular graft's deformed midsection, which was inflated by a 20 mm diameter by 4 cm length Edwards Lifesciences Balloon Catheter. Again the stent's diameter is larger than the vascular grafts diameter in order to create an interference fit between the graft and the stent to prevent the stent from moving or being displaced when subjected to fluid flow. The same general procedures that were used to create the rat sized devices were performed on the larger sized human medical devices (FIG. 37). Consistent and reproducible results on creating the Intravascular Retrievable Cell Delivery System for Islet Transplantation using a variety of ePTFE vascular grafts, CoCr vascular stents, and balloon catheter sizes has been proven. The geometry of the deformation can also be varied and easily controlled with different filling volumes for the balloon catheters and deploying the stents to different ATM pressures based on device specifications.

Figure 39:
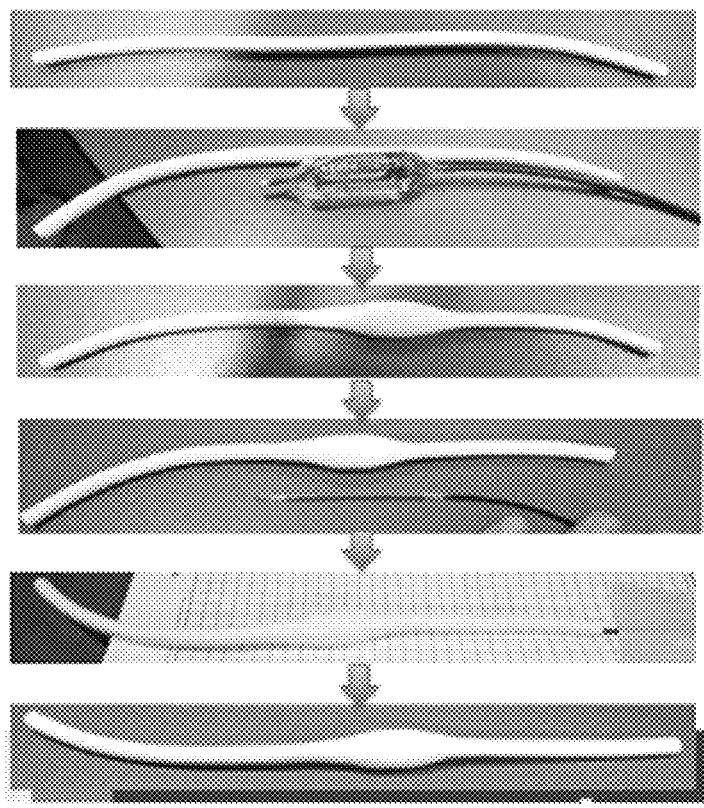
FIG. 39. Images depicting the process that was used to make 'human-sized' ePTFE Intravascular Retrievable Cell Delivery System.
Figure 40:
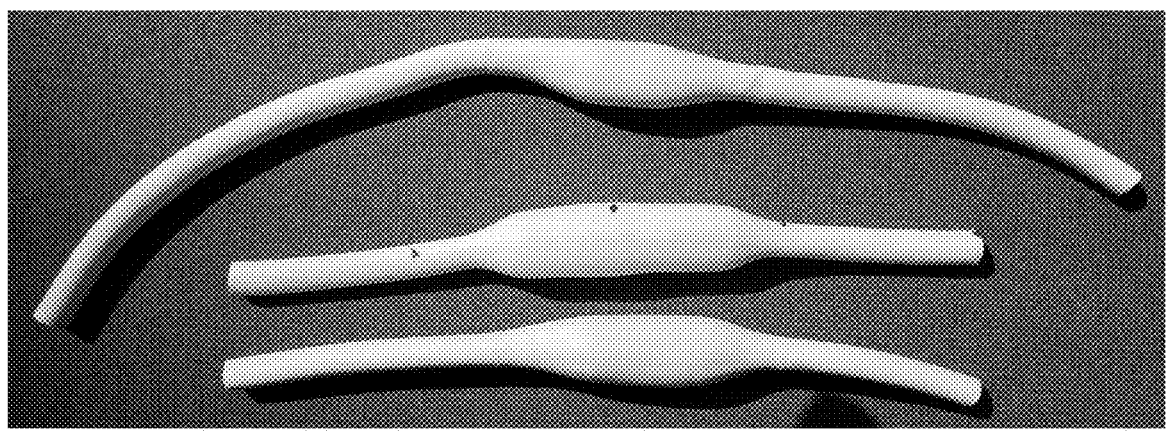
FIG. 40. Image depicting 6 mm inner diameter ePTFE vascular graft systems suitable for AVG implantation in humans, with varying length and deformation dimensions.
Figure 41:
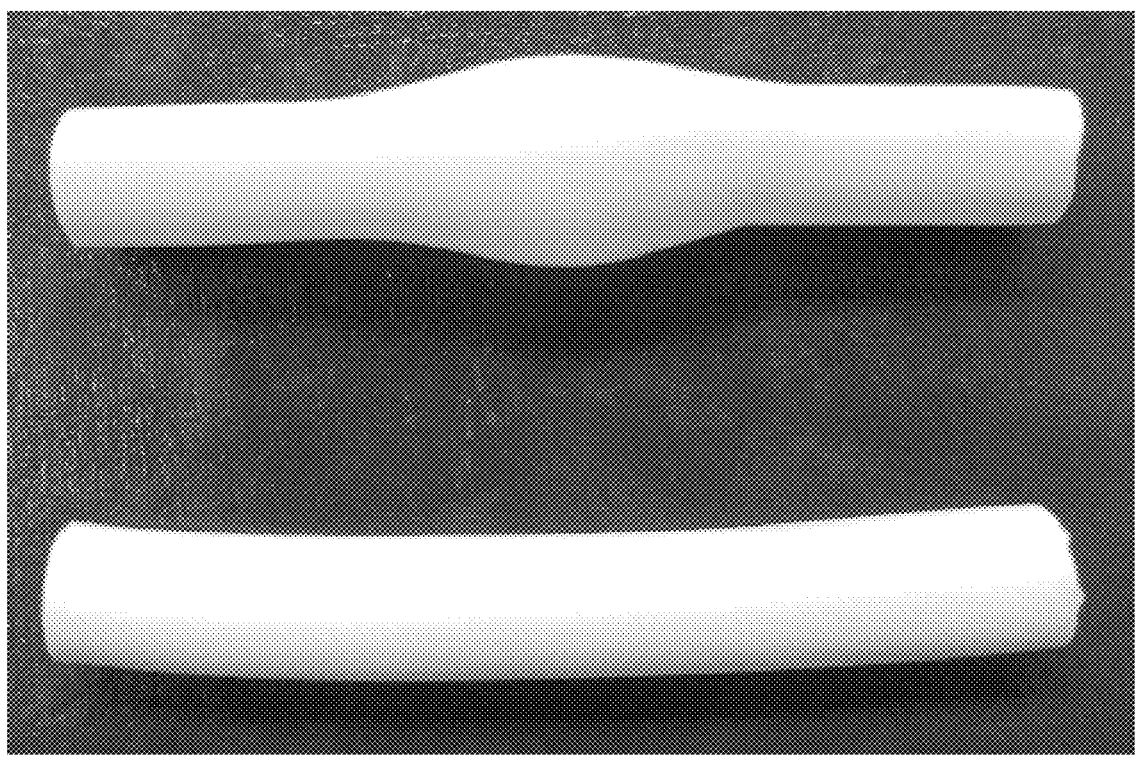
FIG. 41A-D. (A) A 6 mm inner diameter ePTFE vascular graft with a deformed concentric midsection. (B-D) SEM Images of the 6 mm inner diameter undeformed control ePTFE vascular graft (left) and an experimental ePTFE vascular graft that was inflated and deformed by a balloon catheter in the East-West direction (right), at (B) first, (C) second, and (D) third magnifications.
Figure 41:
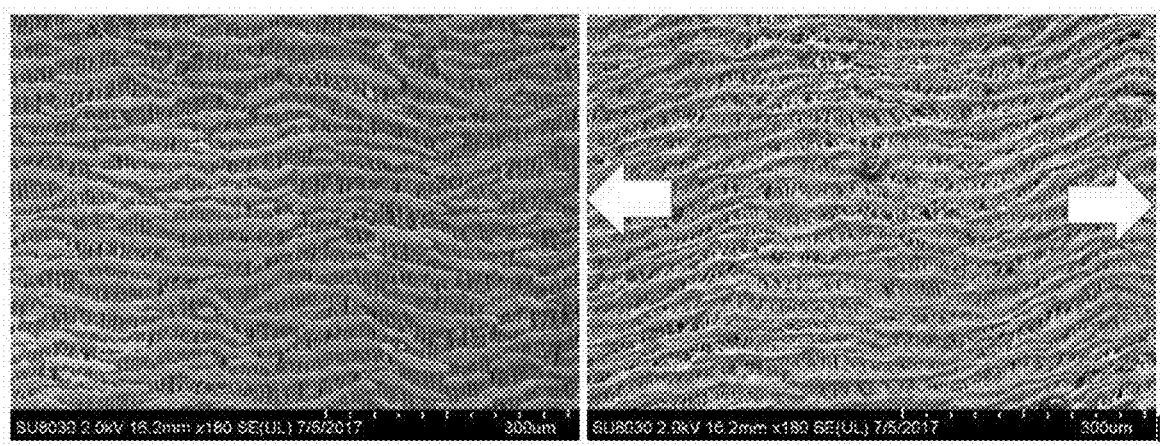
Figure 41:
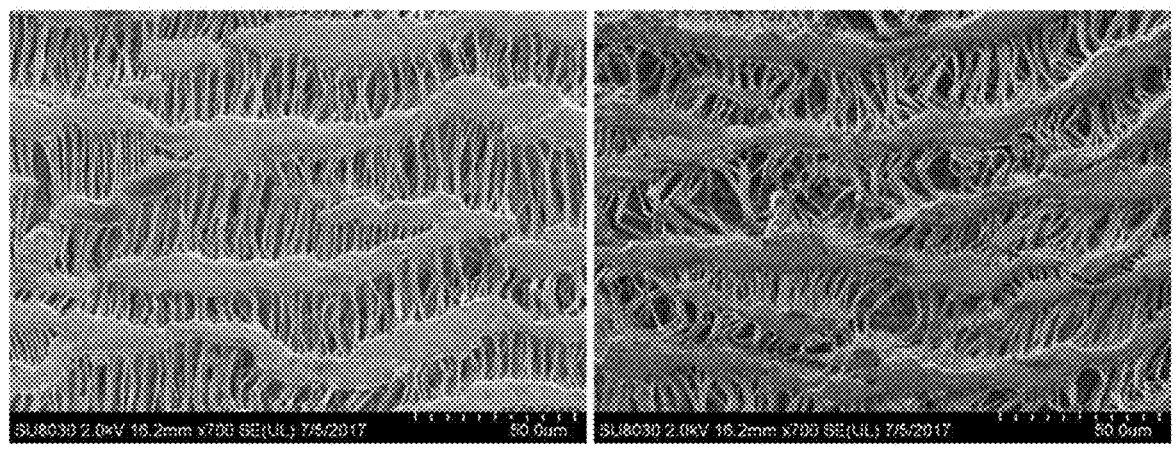
Figure 41:
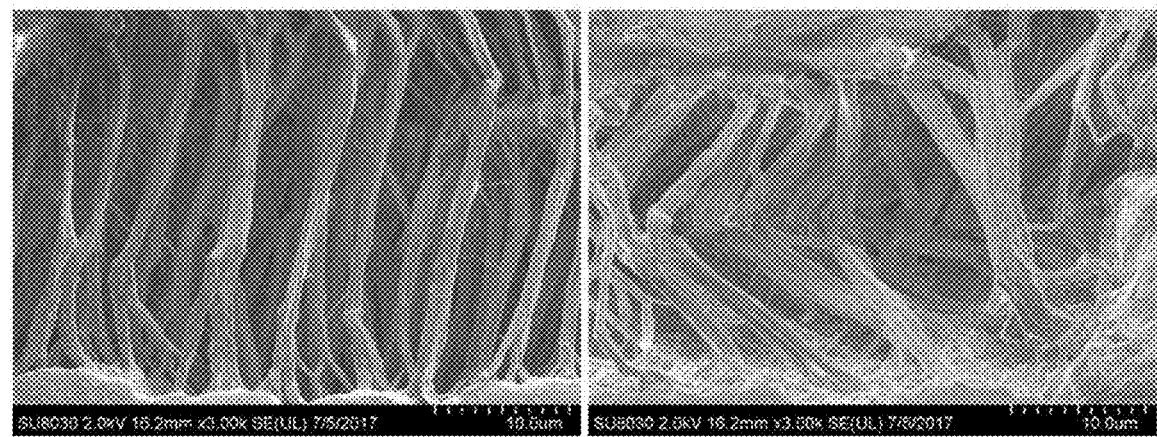
Figure 42:
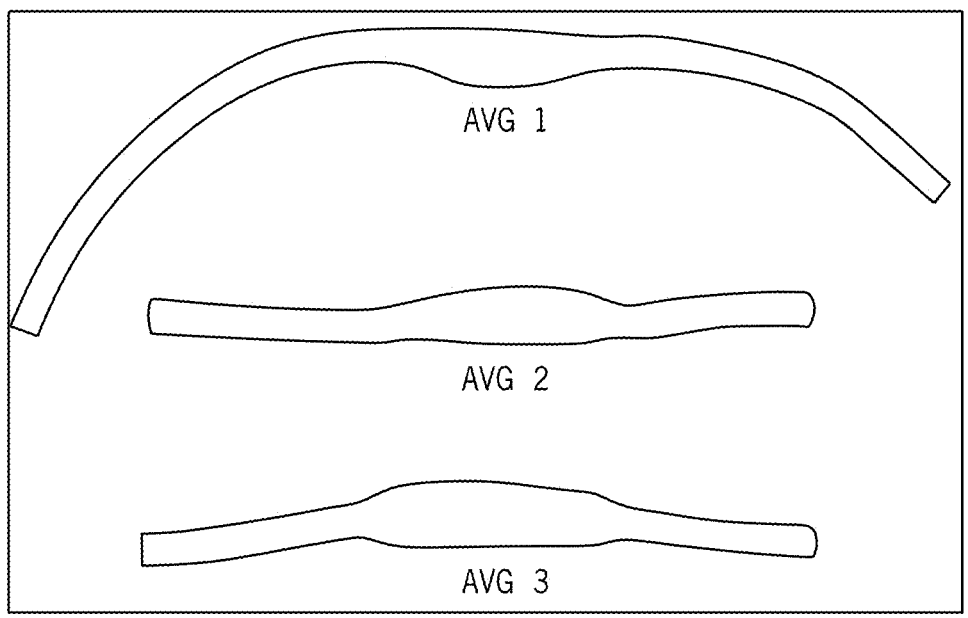
FIG. 42. The top image is a standard photograph of the Human sized Intravascular Retrievable Cell Delivery System for Islet Transplantation labeled by device number accordingly while the bottom is the tomography fluorescent image of the vascular grafts using the IVIS Spectrum fluorescent imaging features. AVG 1 had some PPCN and microsphere solution leak out of the right side of the graft while AVG 2 performed much better, had no leakage, and retained all of the injected solution. The radiant efficiency details the relative abundance of the Fluorescent Green PE Microspheres inside of the vascular graft with yellow to bright red being a large amount of microspheres and the dark red having relatively few microspheres.
Figure 42:
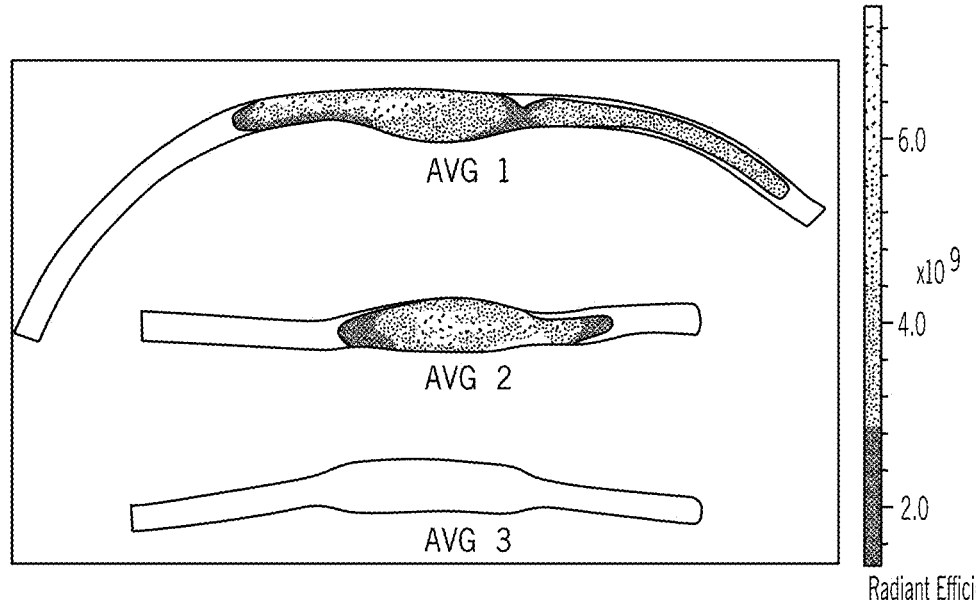
Figure 43:
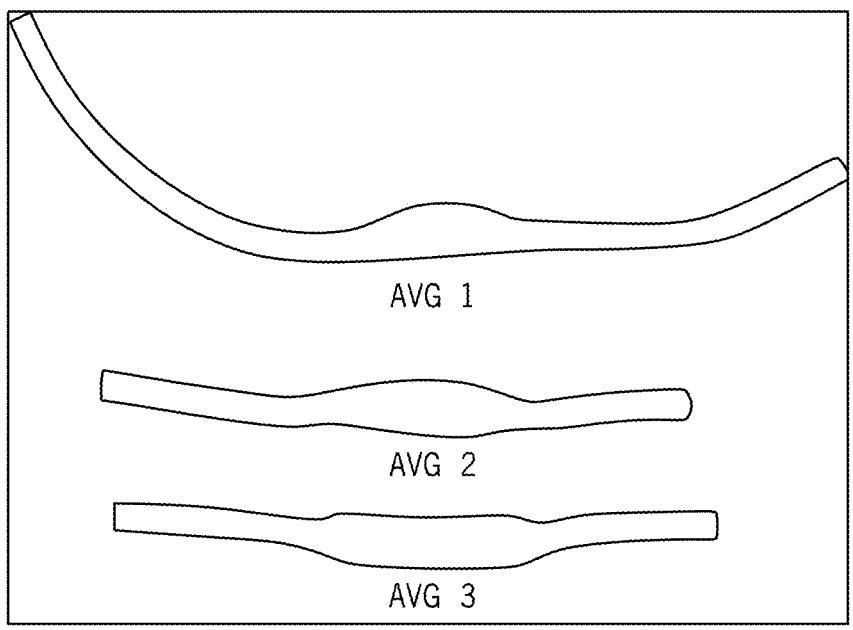
FIG. 43. The Intravascular Retrievable Cell Delivery Systems for Islet Transplantation have been rotated 180 degrees from FIG. 42 in order to provide insight into the filling properties of the injected Fluorescent PE Microspheres and PPCN. The top image is a standard photograph while the bottom image is the tomography fluorescent image of the vascular grafts using the IVIS Spectrum fluorescent imaging features. AVG 1 had some PPCN and microsphere solution leak out of the right side of the graft while AVG 2 performed much better, had no leakage, and retained all of the injected solution.
Figure 43:
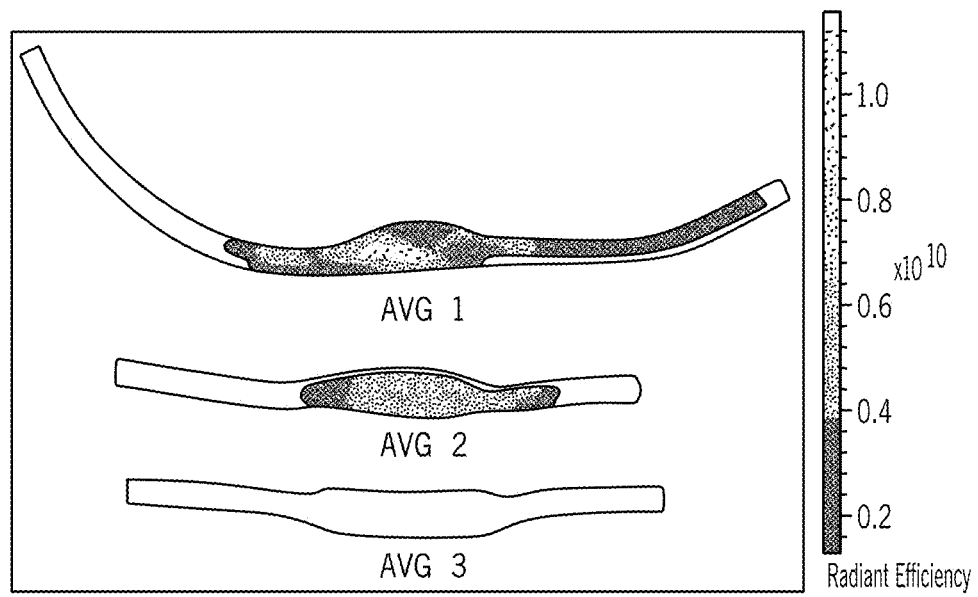
Figure 44:
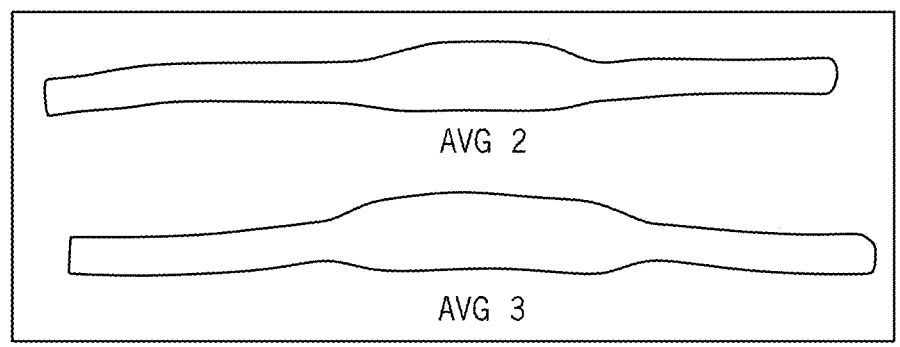
FIG. 44. The top image is a standard photograph of the AVG Intravascular Retrievable Cell Delivery System for Islet Transplantation prototypes labeled accordingly while the bottom is the tomography fluorescent image of the grafts using the IVIS Spectrum fluorescent imaging features. Imaging was performed on AVG 2 alone because this was the best performing injected prototype while AVG 3 serves as the control and did not receive any injected solution. The radiant efficiency details the relative abundance of the Fluorescent Green PE Microspheres inside of the vascular graft prototypes with yellow to bright red being a large amount of microspheres and the dark red having relatively few microspheres in number.
Figure 44:
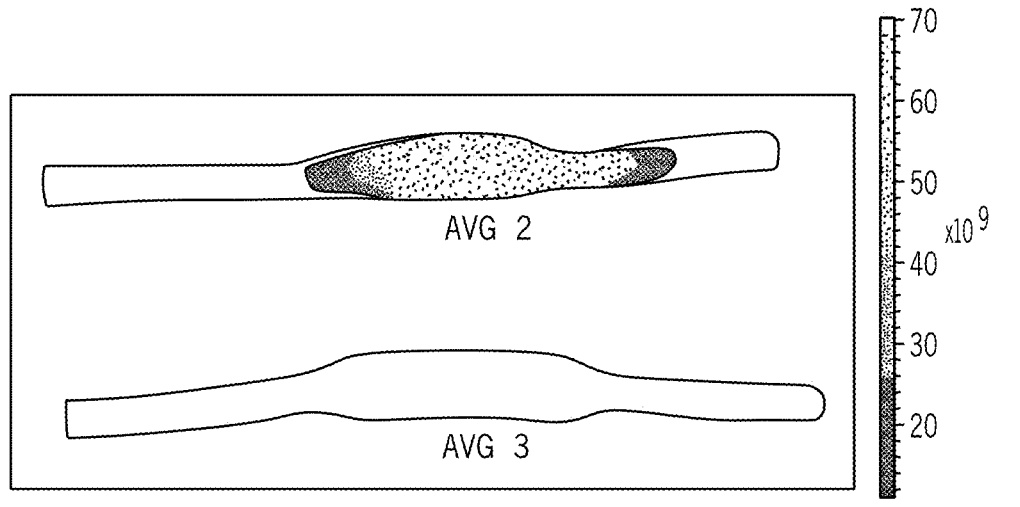
Figure 45:
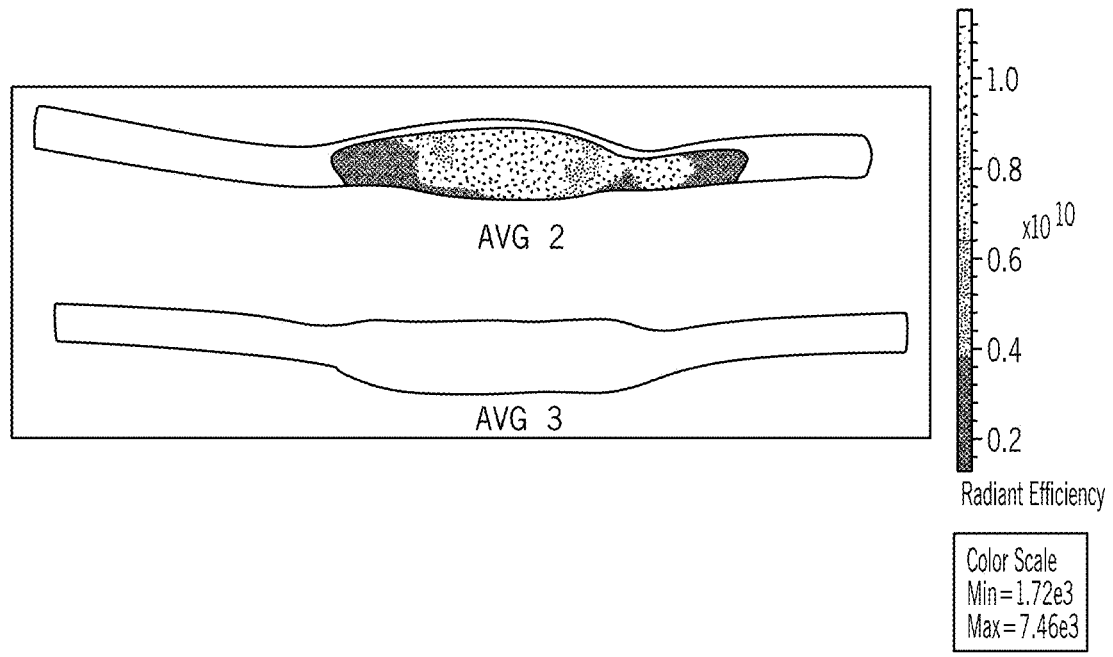
FIG. 45. The vascular grafts have been rotated 180 degrees from FIG. 44 in order to capture the tomography image of the other side of the prototypes and to insure that the filling properties within the Intravascular Retrievable Cell Delivery System for Islet Transplantation are ideal. The radiant efficiency looks largely uniform throughout the entire injected concentric midsection of the vascular graft indicating the success of our injection technique. Moreover, this showcases that the concentric midsection of the implant that we create can retain sufficient volume within their islet storage compartments without additional materials.

A 6 mm inner diameter ePTFE vascular graft with a deformed concentric midsection that was cut and mounted on SEM cylindrical slides for imaging (FIG. 39).

Volume calculations of exemplary 'human-scale' systems and devices (e.g., configured for AVG implantation) and the number of islets that can be safely held within the vascular implant's concentric midsection were calculated (Table 2). The formula that was used first is to calculate the volume that can be accounted for in the medical device's concentric midsection using the volume of a hollow cylinder formula. Next the volume of a human islet equivalent was calculated using the international standard 150 um diameter of a human islet (Shapiro et al. (2000). Islet Transplantation in Seven Patients with Type 1 Diabetes Mellitus Using a Glucocorticoid-Free Immunosuppressive Regimen. New England Journal of Medicine, 343(4), 230-238; herein incorporated by reference in its entirety). The volume in the graft was divided by a standard human islet's volume to yield the number of human islets that could be stored in the devices concentric midsection without any additional additives.

TABLE 2

Calculations for the volume and the injected material properties for the AVG Intravascular Retrievable Cell Delivery System for Islet Transplantation prototypes before characterization with IVIS Spectrum imaging.

| Prototype Number | Calculated Volume of Concentric Midsection (mL) | Total Volume of PPCN and Microspheres Injected (mL) | Volume of Injected PPCN (mL) | Volume of Injected Islets (mL) | Number of Injected Microsphere Islet Equivalents | Weight of Syringe Empty (g) | Weight of Syringe Full (g) | Weight of Vascular Implant Empty (g) | Weight of Vascular Implant Full (g) |
|---|---|---|---|---|---|---|---|---|---|
| AVG 1 | 1.905 | 1.9 | 0.95 | 0.95 | 537,634 | 3.53 | 5.45 | 41.63 | 43.33 |
| AVG 2 | 2.704 | 2.7 | 1.2 | 1.5 | 848,896 | 3.58 | 6.38 | 33.28 | 36.06 |
| AVG 3 | 3.848 | Control graft not injected with PPCN or Microspheres | NA | NA | NA | NA | NA | NA | NA |

Experiments with injecting PPCN hydrogel and Fluorescent Green Polyethylene (PE) Microspheres into 'human-scale' systems were performed. Fluorescent Green PE Microspheres, 125-150 μm in diameter, were injected in conjugation with PPCN to simulate islets in solution. Fluorescent PE Microspheres also have the benefit of being detected and imaged by an IVIS Spectrum Bioluminescence/Fluorescence Imaging System. Injections were performed with a syringe directly into the bottom of the concentric midsection of the vascular grafts at a 45° angle. The two open ends of the Intravascular Retrievable Cell Delivery System where held vertically upright during the injection process. Once the PPCN and microsphere solution injection was complete the grafts were stored in an incubator at 37° C. The volume of the injected material was based on the dimensions of the vascular graft prototypes that determined its concentric midsection storage volume (Table 2). IVIS Spectrum imaging followed a two-step procedure where first a standard photograph of the AVG Intravascular Retrievable Cell Delivery System for Islet Transplantation was taken followed by a fluorescent image specifically targeting the excitation and emission range of the Fluorescent Green PE Microspheres (FIGS. 40-43). The radiant efficiency to the right of the fluorescent images details the relative abundance of the Fluorescent Green PE Microspheres inside of the vascular graft prototypes with yellow to bright red being a higher amount of microspheres and the dark red having relatively few microspheres in number.

REFERENCES

The following references are herein incorporated by reference in their entireties.

Shapiro, A. J., Lakey, J. R., Ryan, E. A., Korbutt, G. S., Toth, E., Warnock, G. L., Rajotte, R. V. (2000). Islet Transplantation in Seven Patients with Type 1 Diabetes Mellitus Using a Glucocorticoid-Free Immunosuppressive Regimen. The New England Journal of Medicine, 343(4), 230-238.

Sharpio, A. J., Ricordi, C., Hering, J. B., Auchincloss, H., Lindblad, R., Robertson, R. P., Secchi, A., Brendel, D. M., Berney, T. Brennan, C. D., Cagliero, E., Alejandro, R., Ryan, E. A., DiMercurio, B., Morel, P., Polonsky, S. K., Reems, J., Bretzel, G. R., Bertuzzi, F., Froud, T., Kandaswamy, R., Sutherland, E. R. D., Eisenbarth, G., Segal, M., Preiksaitis, J., Korbutt, S. G., Barton, B. F., Viviano, L., Seyfert-Margolis, V., Bluestone, J., and Lakey, R. T. J., (2006). International Trial of the Edmonton Protocol for Islet Transplantation. The New England Journal of Medicine, 355(13), 1318-1330.

Ryan, E. A., Paty, B. W., Senior, P. A., Bigam, D., Alfadhli, E., Kneteman, N. M., Shapiro, A. J. (2005). Five-Year Follow-Up After Clinical Islet Transplantation. Diabetes, 54(7), 2060-2069.

The invention claimed is:

1. A device for the intravascular transplantation of cells comprising:
   (a) an outer graft, the outer graft comprising an inner lumen and an outer wall, wherein the outer graft comprises first and second terminal portions and a central expanded portion, the central portion having a greater inner cross-sectional area than the terminal portions;
   (b) an inner vascular stent, the inner vascular stent comprising an inner lumen and a semi-permeable outer wall;
   wherein the inner vascular stent comprises a cross-sectional size and shape along its entire length that allows the inner vascular stent to fit within the lumen of the outer graft; and
   wherein the inner vascular stent is configured for insertion into the inner lumen of the outer graft, and wherein when the inner vascular stent resides within the outer graft, a void exists between all or a portion of the inner vascular stent and all or a portion of the outer graft;
   (c) a carrier material within the void between the inner vascular stent and the outer graft; and
   (d) cells entrapped within the carrier material; wherein the cells are selected from islets cells, stem cells, hepatocytes, and renal tubular cells; and
   (e) a therapeutic agent within the carrier material, wherein the therapeutic agent is selected from insulin, a hormone, and an anticoagulant; wherein the semi-permeable outer wall is (i) configured to allow fluids, nutrients, peptides, and proteins to pass between the inner lumen of the inner vascular stent and the void between the inner vascular stent and the outer graft, and (ii) configured to contain the cells within the void.

2. The device of claim 1, wherein when the inner vascular stent resides within the outer graft, the inner vascular stent extends from the first terminal portion of the outer graft to the second terminal portion of the outer graft.

3. The device of claim 2, wherein the outer wall of the inner vascular stent contacts the terminal portions of the outer graft, and wherein the inner lumen of the outer graft and the outer wall of the inner vascular stent are configured to interact to hold the inner vascular stent in place within the outer graft.

4. The device of claim 1, wherein the inner lumen of the inner vascular stent is configured to allow blood to flow through the inner lumen, when inserted into the vasculature of a subject.

5. The device of claim 1, wherein the inner vascular stent is permeable to insulin.

6. The device of claim 1, wherein the carrier material is a biocompatible polymer-based material.

7. The device of claim 6, wherein the carrier material comprises a thermoresponsive polymer.

8. The device of claim 7, wherein the carrier material comprises poly (polyethyleneglycol citrate-co-N isopropylacrylamide) (PPCN).

9. The device of claim 1, wherein the cells are pancreatic islet cells and the inner vascular stent is permeable to insulin.

10. The device of claim 1, further comprising endothelial cells adhered to the inner lumen of the inner vascular stent.

11. A method comprising implanting a device of claim 1 into the vasculature of a subject.

* * * * *